US010039685B2

(12) United States Patent
Wu et al.

(10) Patent No.: US 10,039,685 B2
(45) Date of Patent: Aug. 7, 2018

(54) PASSIVE POWER-CONSERVATIVE ARTIFICIAL KNEE

(71) Applicant: THE REGENTS OF THE UNIVERSITY OF CALIFORNIA, Oakland, CA (US)

(72) Inventors: Shang-Li Wu, Berkeley, CA (US); Homayoon Kazerooni, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/190,946

(22) Filed: Jun. 23, 2016

(65) Prior Publication Data

US 2016/0374887 A1      Dec. 29, 2016

Related U.S. Application Data

(60) Provisional application No. 62/183,440, filed on Jun. 23, 2015.

(51) Int. Cl.
*A61F 2/64* (2006.01)
*A61H 1/02* (2006.01)
(Continued)

(52) U.S. Cl.
CPC .............. *A61H 1/0262* (2013.01); *A61F 2/64* (2013.01); *A61F 2/68* (2013.01); *A61F 5/0123* (2013.01);
(Continued)

(58) Field of Classification Search
CPC .. A61F 2/64; A61F 5/01; A61F 5/0123; A61F 5/0125; A61F 2005/0158
(Continued)

(56) References Cited

U.S. PATENT DOCUMENTS 5,201,776 A * 4/1993 Freeman ................. A61F 2/644
602/26
5,399,149 A * 3/1995 Frankowiak .......... A61F 5/0125
16/326

(Continued)

OTHER PUBLICATIONS

International Search Report and Written Opinion issued in the corresponding application PCT/US16/39004 dated Sep. 16, 2016.
(Continued)

*Primary Examiner* — Bruce E Snow
(74) *Attorney, Agent, or Firm* — Kwan & Olynick LLP

(57) ABSTRACT

A passive artificial knee comprises first and second links rotatably coupled at a knee joint, a passive compressive force generator rotatably coupled to the second link, and a release mechanism coupled to the first link. When a relative angle of the first and second links is less than a toggle angle, the release mechanism locks in a first operational mode, and the force generator compresses, resisting the flexing of the second link relative to the first link. When the relative angle is larger than the toggle angle, the force generator decompresses and encourages the flexion of said second link relative to said first link. When the force generator is substantially extended and said compressive force is substantially small, the release mechanism moves into a second operational mode, wherein the force generator neither resists nor encourages the extension and flexion of said second link from said first link.

10 Claims, 42 Drawing Sheets

(51) Int. Cl.
  *A61F 5/01* (2006.01)
  *A61F 2/68* (2006.01)
  *A61H 3/00* (2006.01)

(52) U.S. Cl.
  CPC .......... *A61F 5/0127* (2013.01); *A61H 1/024* (2013.01); *A61H 3/00* (2013.01); *A61F 2005/0155* (2013.01); *A61F 2005/0158* (2013.01); *A61H 1/0244* (2013.01); *A61H 2201/1207* (2013.01); *A61H 2201/1246* (2013.01); *A61H 2201/149* (2013.01); *A61H 2201/164* (2013.01); *A61H 2201/165* (2013.01); *A61H 2201/1628* (2013.01); *A61H 2201/1676* (2013.01)

(58) Field of Classification Search
  USPC ........................................ 602/26; 623/41–46
  See application file for complete search history.

(56) References Cited

U.S. PATENT DOCUMENTS

| | | |
|---|---|---|
| RE37,209 E | 6/2001 | Hensley et al. |
| 6,635,024 B2 | 10/2003 | Hatton et al. |
| 7,393,335 B2 | 7/2008 | Carvey et al. |
| 7,410,472 B2 | 8/2008 | Yakimovich et al. |
| 2002/0094919 A1 | 7/2002 | Rennex et al. |
| 2003/0153854 A1 | 8/2003 | Nijenbanning et al. |
| 2006/0241539 A1* | 10/2006 | Agrawal ................ B25J 9/0006 602/23 |
| 2007/0232972 A1 | 10/2007 | Martinez |
| 2012/0071803 A1 | 3/2012 | Jansson |
| 2013/0006388 A1* | 1/2013 | Pusch ...................... A61F 2/64 623/43 |
| 2013/0190669 A1 | 7/2013 | Rokosz et al. |
| 2013/0268093 A1 | 10/2013 | Gilbert et al. |
| 2014/0276304 A1 | 9/2014 | Dollar et al. |
| 2015/0230962 A1* | 8/2015 | Auberger ............... A61F 5/0123 602/26 |

OTHER PUBLICATIONS www.capstoneorthopedic.com—Capstone Orthopedic: Quality Orthopedic Services, 3 pages, dated Jun. 21, 2016.
www.oandp.com—Sensor Walk Electronic Stance Control, 2 pages, dated Jun. 23, 2016.
http://www.ottobockus.com—The Free Walk stance control orthosis, 1 page, dated Jun. 21, 2016.
"Int'l Application Serial No. PCT/US160/39004, Int'l Preliminary Report on Patentability dated Jan. 4, 2018", 7 pages.

* cited by examiner

PASSIVE POWER-CONSERVATIVE ARTIFICIAL KNEE

FIELD OF THE INVENTION

The present invention pertains to the art of artificial lower limb prosthetics and orthotic systems: more particularly, to a passive power-conservative artificial knee that can be used for a variety of orthotic applications.

BACKGROUND ART

A traditional knee-ankle-foot orthosis (KAFO) is used to increase the patient stability during the weight-bearing phase of walking. A traditional KAFO locks the knee in full extension, which provides stability. This locked posture results in patients' ability to ambulate with gait deviations that can lead to overuse injuries. A stance control orthosis (SCO) allows a user's knee to flex during a swing phase of a gait cycle, and prevents knee flexion for stability during the stance phase. By allowing the knee to bend during the swing phase, SCOs allow a more natural gait, which may reduce secondary complications from gait compensations and allow the user to walk with less effort.

In general, stance control orthoses are known. By way of example, U.S. Patent Application Publication No. 2003/0153854 to Fillauer teaches a gravity-actuated knee joint locking system for a Swing Phase Lock (SPL) orthosis. The Swing Phase Lock orthosis uses a simple internal pendulum mechanism mounted on a thigh link (the member that moves in unison with the user's thigh). As the thigh link moves, the pendulum swinging motion locks and unlocks a shank link (the member that moves in unison with the user's shank) relative to the thigh link. This allows for locking and unlocking of the knee joint for different phases of a walking cycle.

By way of another example, a stance control orthosis by Ottobock (FreeWalk) and a knee-ankle-foot orthosis by Becker (UTX) work based on a similar principle. That is, dorsiflexion of a foot at the end of a stance phase pulls on a controllable cable connected to a locking mechanism at a knee joint. This pulling action disengages the locking mechanism to enable swing. The locking mechanism is spring loaded and locks the knee when the knee is fully extended.

In another example, an orthosis by Ottobock (Sensor Walk) uses a wrap spring at a knee joint for locking and unlocking the knee. This orthosis includes two sets of sensors: one at the knee to measure a knee angle and another at a footplate to measure force between the foot and the floor. The orthosis further includes a wrap spring clutch replacing a lateral knee joint to provide braking capability to support the anatomic knee joint; a microprocessor-controlled release for the brake; electronic circuitry; and a battery pack carried in a waist pack. Sensors in the footplate disengage the wrap spring clutch and allow the knee to bend in the late stance phase, when weight has been transferred to the contralateral side and is ready for single-limb support. A knee sensor senses extension of the knee after toe off and sends a signal to the microprocessor putting the wrap spring clutch in its locked position.

A Horton Stance Control Orthosis taught by U.S. Pat. No. 6,635,024 includes a locking mechanism that locks and unlocks the knee with the help of a push rod. The push rod is placed between the heel and the knee. The push rod locks the knee at heel strike and unlocks the knee right at the end of stance phase. The device locks knee at any angle.

In view of the devices discussed above, there remains a need to provide a stance control orthosis which can be simply and economically constructed, and which assists a wearer during walking. There is also a need for an orthosis device which does not require sensors or an electrical power source to operate.

SUMMARY OF INVENTION

The present invention is directed to a passive power-conservative artificial knee. In particular, the invention here describes an artificial knee and its applications in a variety of exoskeleton systems where a passive force generator (e.g., a spring actuator) is used to impede the knee flexion during early stance (an early portion of a stance phase). Energy during a portion of the stance phase is stored in the passive force generator and then released at late stance (a later portion of the stance phase) to provide sufficient flexion during swing (swinging of the leg) to clear the ground. The device is composed of a thigh link and a shank link rotatably coupled to each other at a knee joint. A passive compressive force generator (e.g., a gas spring actuator) is rotatably coupled to either the shank link or the thigh link from its first end. When the shank link is flexing toward the thigh link during stance (stance phase) and an angle of the shank link relative to the thigh link is less than a predetermined toggle angle, the force generator is becoming compressed (energy is stored) and resists the flexion of the shank link relative to the thigh link. When the shank link is flexing toward the thigh link and the angle of shank link relative to the thigh link is larger than the toggle angle, the compressive force generator becomes decompressed (energy is released) and therefore encourages the flexion of the shank link relative to the thigh link. When the force generator is substantially extended and the compressive force is substantially small toward the end of flexion during a swing phase, the force generator neither resists nor encourages the extension and flexion of the shank link from the thigh link. This means the shank link can freely extend during swing. The artificial knee described herein may be worn not only independently on a wearer's knee, but also in conjunction with hip, ankle or foot exoskeletons. This gives a great deal of flexibility for use of exoskeleton knees in a variety of medical, civilian and military applications.

DESCRIPTION OF EMBODIMENTS

Figure 1:
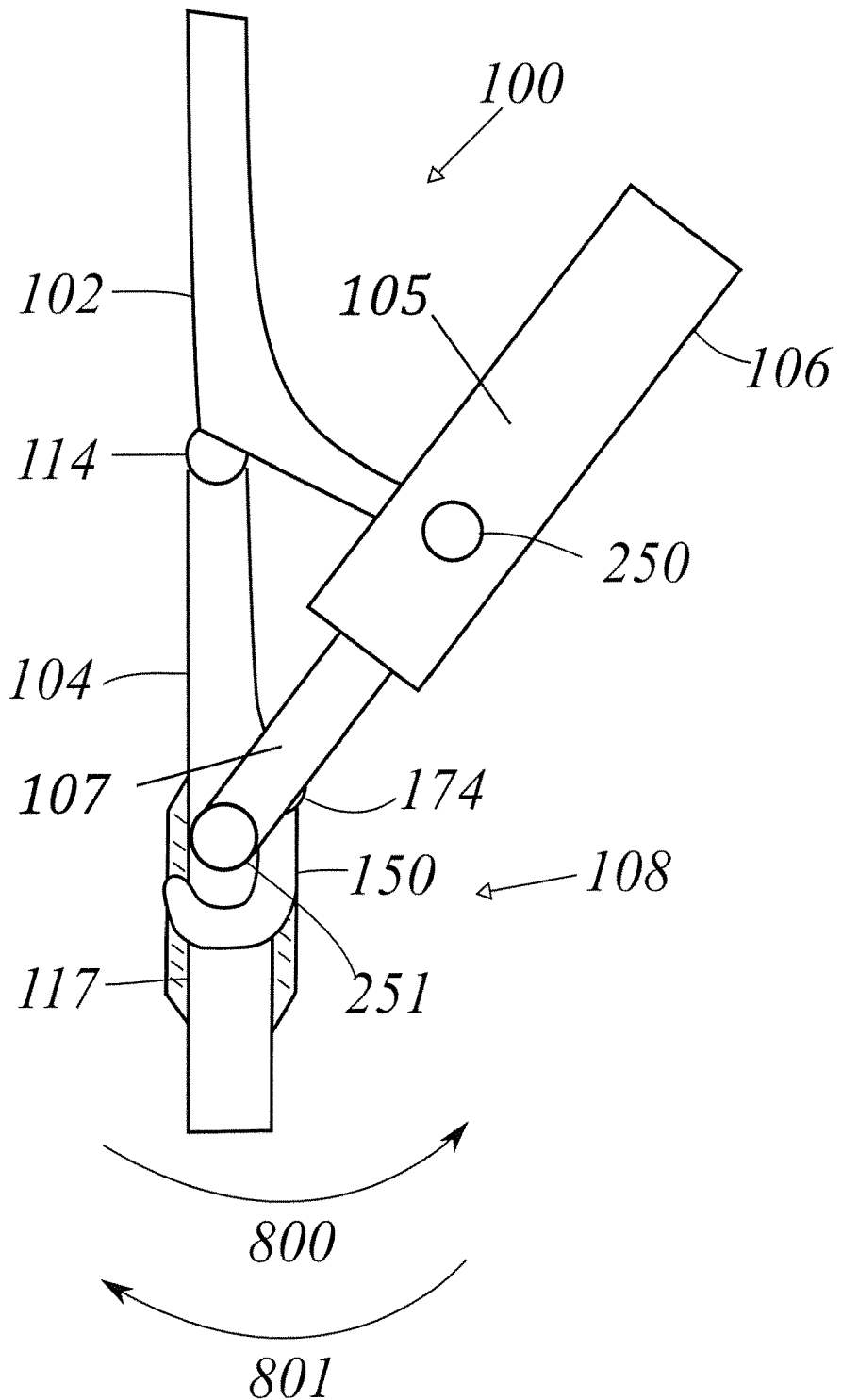
FIG. 1 depicts an embodiment of the passive power-conservative artificial knee of the present invention.

FIG. 1 shows an embodiment of a passive power-conservative artificial knee 100 which is configured to be coupled to a lower extremity of a person 200. FIG. 1 shows the passive power-conservative artificial knee 100 without a person 200 (depicted later in FIGS. 37-40). Passive power-conservative artificial knee 100, among other things, comprises a thigh link 102, a shank link 104, a compressive force generator 106, and a release mechanism 108. Shank link 104 is rotatably coupled to thigh link 102 along knee joint 114.

Figure 32:
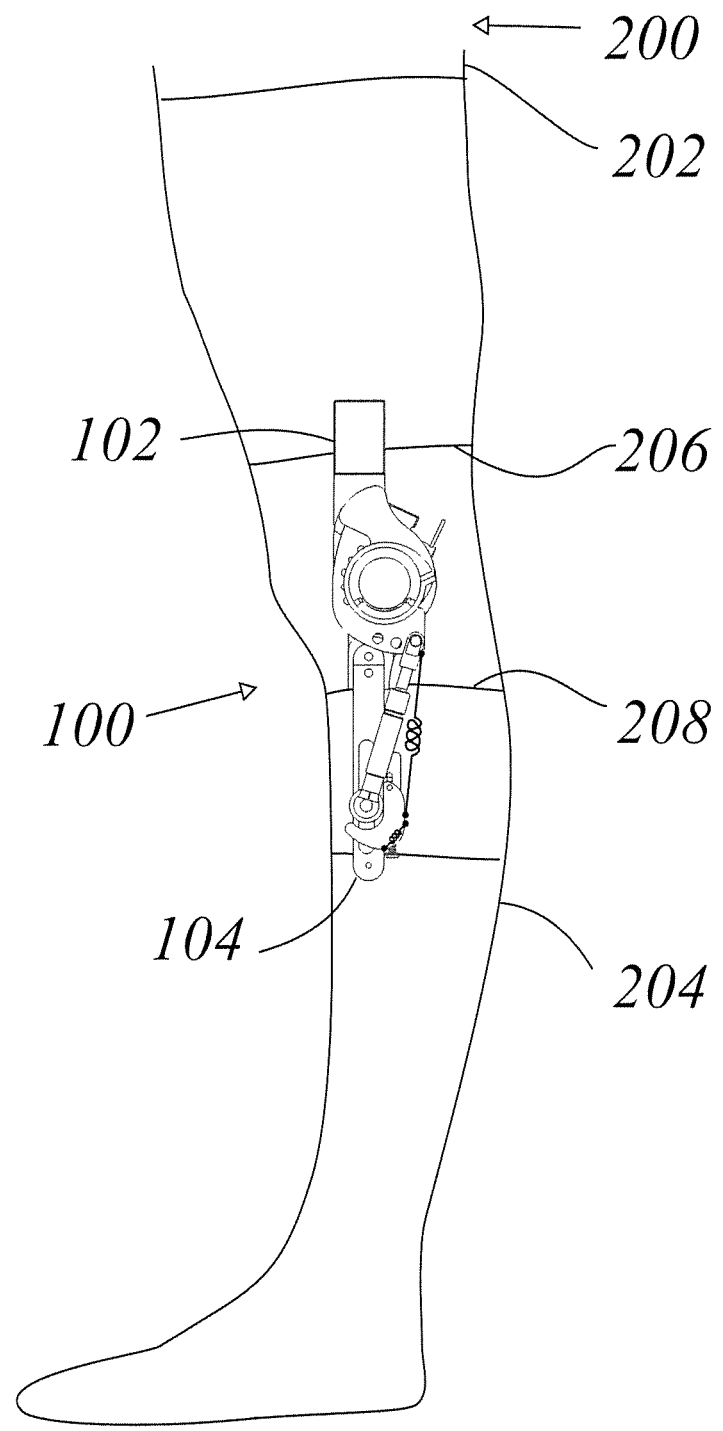
FIG. 32 shows an embodiment of the invention wearing by a person 200.

In some embodiments of the invention, as shown in FIG. 32, thigh link 102 is configured to move in unison with a user's thigh 202. In some embodiments of the invention, shank link 104 is configured to move in unison with a user's shank 204. In some embodiments of the invention, passive power-conservative artificial knee 100 further comprises a thigh connector 206 that allows coupling to a user's thigh 202, and a shank connector 208 that allows coupling to a user's shank 204. In some embodiments of the inventions thigh connector 206 and shank connector 208 comprise braces. Although braces have been used to demonstrate the coupling of shank link 104 and thigh link 102 to the user's thigh 202 and user's shank 204 in FIG. 32, an ordinary person skilled in the art would understand that many methods and devices can be employed that would cause shank link 104 and thigh link 102 to move in unison with user's shank 204 and user's thigh 202. The coupling through shank and thigh braces is not the only method of causing the unison movement contemplated for use with the invention.

In the embodiment of FIG. 1, passive compressive force generator 106 is in the form of a strut actuator including a hollow case or cylinder 105, a rod 107 extending therefrom, and an internal means for providing compression forces, such as a spring or compressed air (not shown). Passive compressive force generator 106 is rotatably coupled to thigh link 102 from a first attachment point or end 250 on cylinder 105. Force generator 106 is capable of generating a compressive force between its first attachment end 250 and its second attachment point or end 251 (hereinafter ends 250, 251). One of ordinary skill in the art would understand that ends 250, 251 of force generator 106 are moveable with respect to one another and that force generator 106 includes a means for resisting movement of ends 250, 251 towards one another, such as a spring. Thus, both ends (250, 251) of force generator 106 resist movement toward each other (provide resistance force) when both ends 250 and 251 are pushed toward to each other. The resistance force that tries to keep first end 250 and second end 251 away from each other is called compressive force. One of ordinary skill in the art would understand that different types of passive compressive force generators may be utilized with the present invention. In some embodiments of the invention, passive compressive force generator 106 is a gas spring as shown in FIG. 1. In some embodiments of the invention, passive compressive force generator 106 is an air spring. In some embodiments of the invention, passive compressive force generator 106 is a compression coil spring. A common characteristic among all embodiments of passive compressive force generators is that both ends (250, 251) of force generator 106 resist the movement of the ends toward each other when both ends 250 and 251 are pushed toward to each other.

In the embodiment of FIG. 1, a release mechanism 108 is coupled to shank link 104. Release mechanism 108 has at least two operational modes. In its first operational mode, release mechanism 108 rotatably couples second end 251 of force generator 106 to shank link 104. This means release mechanism 108 allows the compressive force to be imposed on shank link 104. In its second operational mode, release mechanism 108 does not couple second end 251 of force generator 106 to shank link 104. This means release mechanism 108, in this second operational mode, does not allow the compressive force of force generator 106 to be imposed on shank link 104. The manner in which the embodiment of FIG. 1 transitions between first and second operational modes will be discussed in more detail below.

Figure 3:
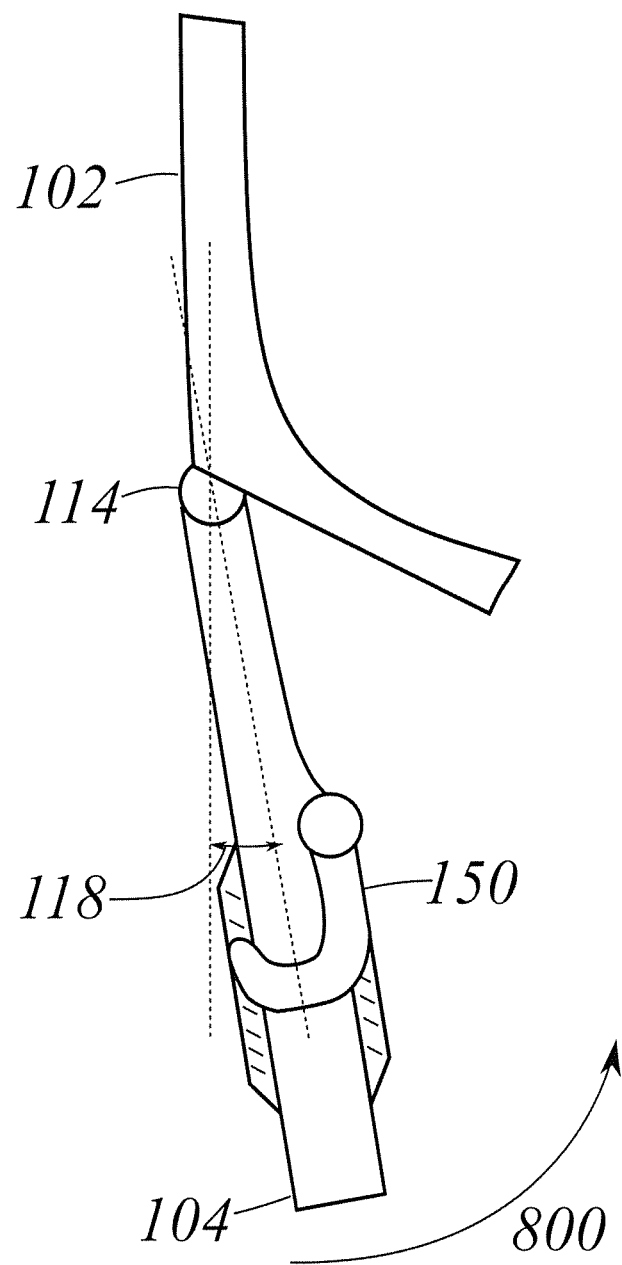
FIG. 3 depicts a knee angle 118 of a shank link 104 relative to a thigh link 102 where other parts have been removed for clarity.
Figure 17:
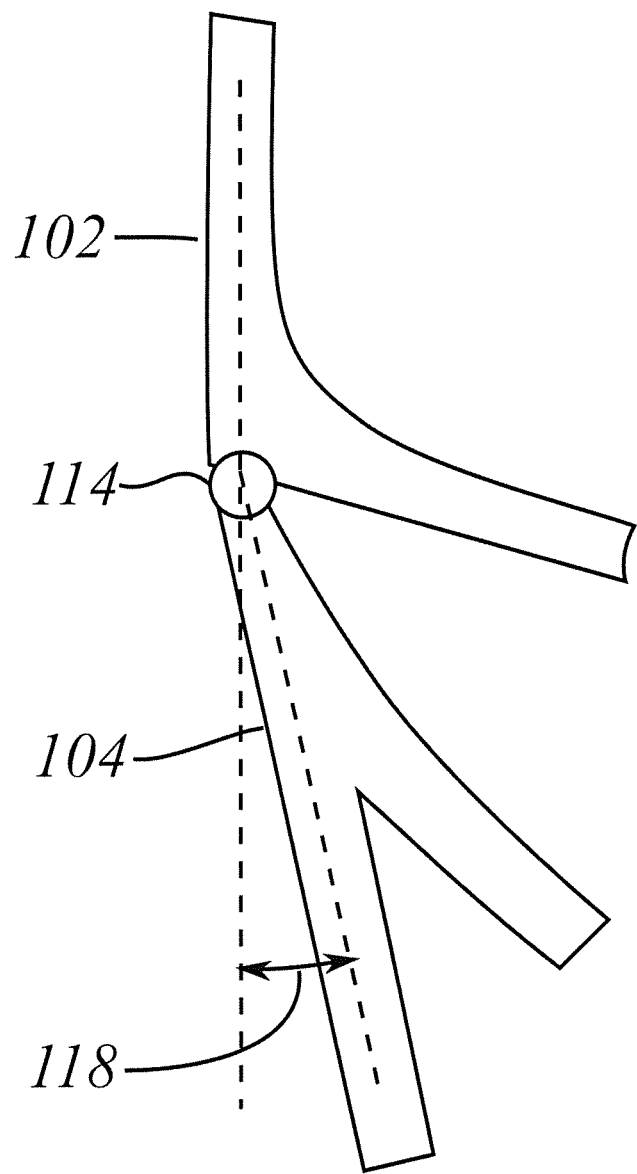
FIG. 17 depicts knee angle 118, the angle of shank link 104 relative to thigh link 102, where other parts have been removed for clarity in the second embodiment.

As shown in FIGS. 3 and 17, a knee angle 118 representing the angle of shank link 104 relative to thigh link 102, shows how much shank link 104 has flexed toward thigh link 102 along arrow 800. That is, knee angle 118 represents an angle between an imaginary longitudinal line extending through a length of thigh link 102 and a pivot point of knee joint 114, and an imaginary longitudinal line extending through a length of shank link 104 and the pivot point of knee joint 114.

Figure 2:
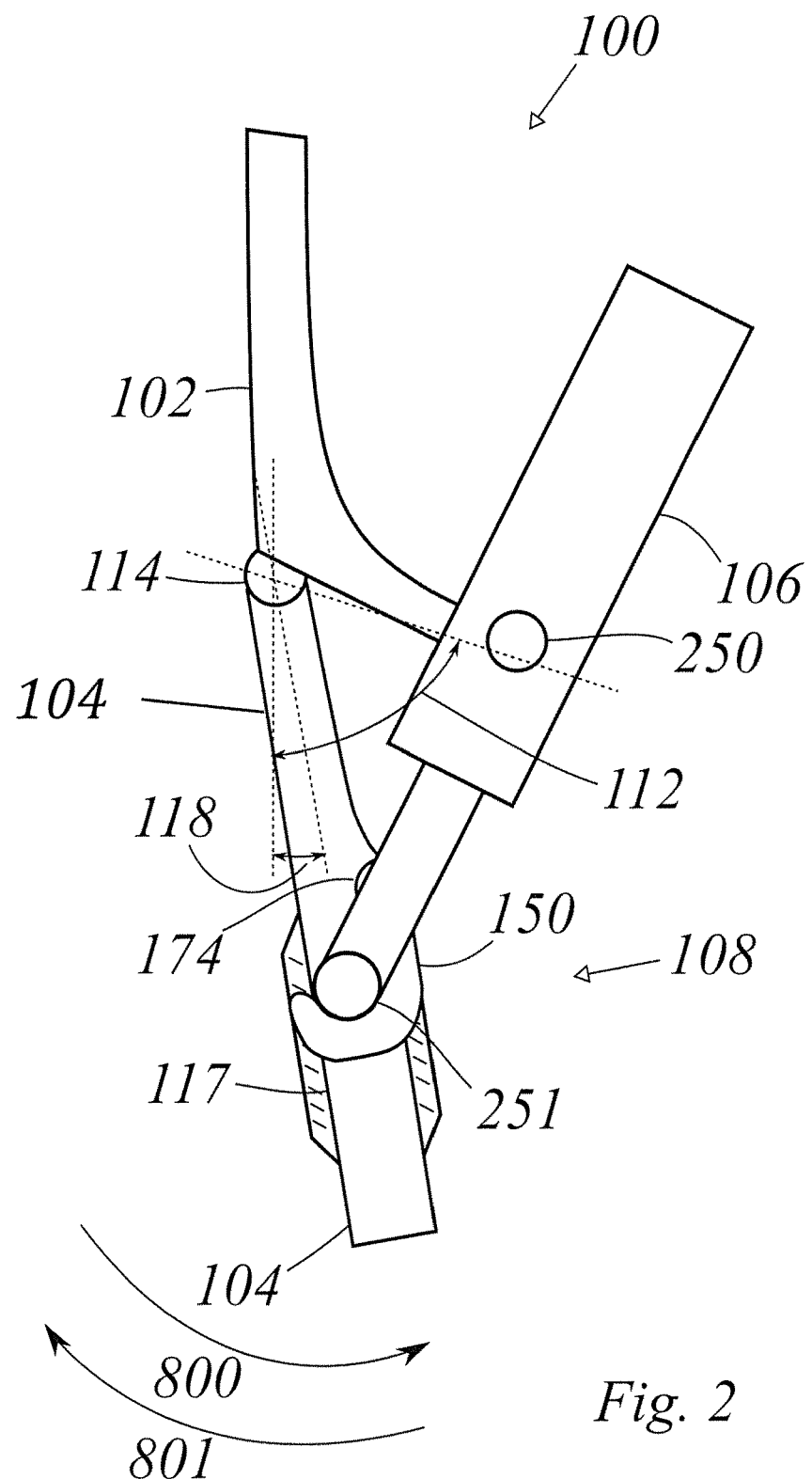
FIG. 2 depicts an embodiment of the invention where a release mechanism 108 is in its first operational mode such that force generator 106 provides a torque on a shank link 104 relative to a thigh link 102 along a direction 801.
Figure 4:
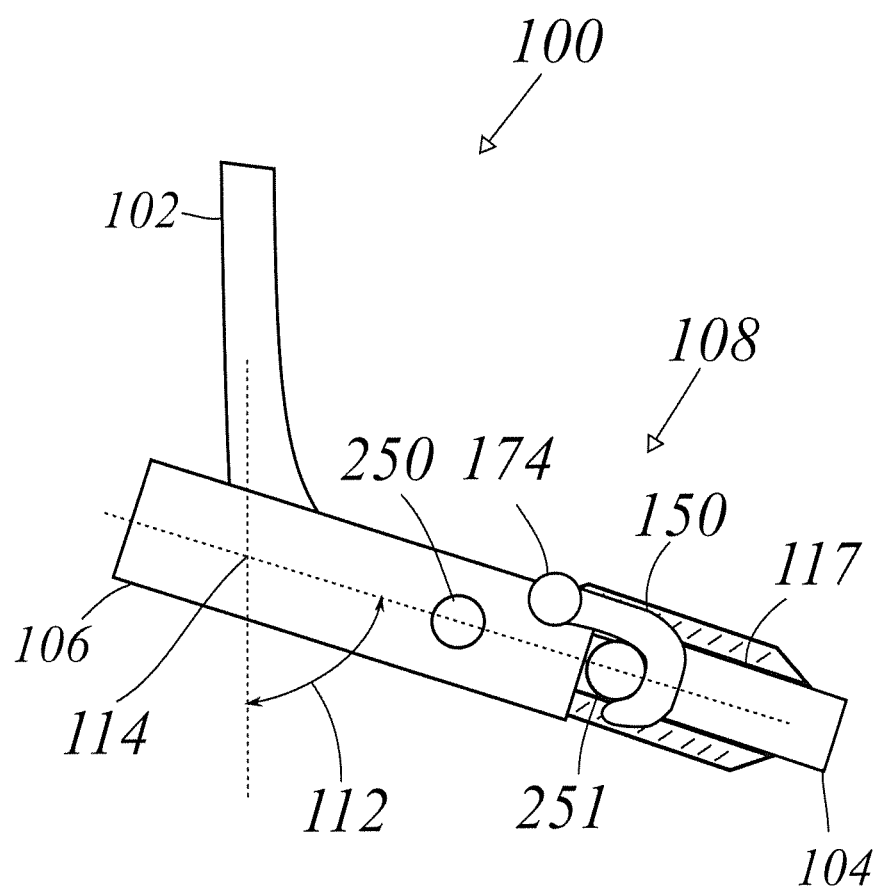
FIG. 4 shows an embodiment of the invention where an angle of a shank link 104 relative to a thigh link 102 is equal to a toggle angle 112 such that a force generator 106 does not provide torque on the shank link 104 relative to the thigh link 102.
Figure 5:
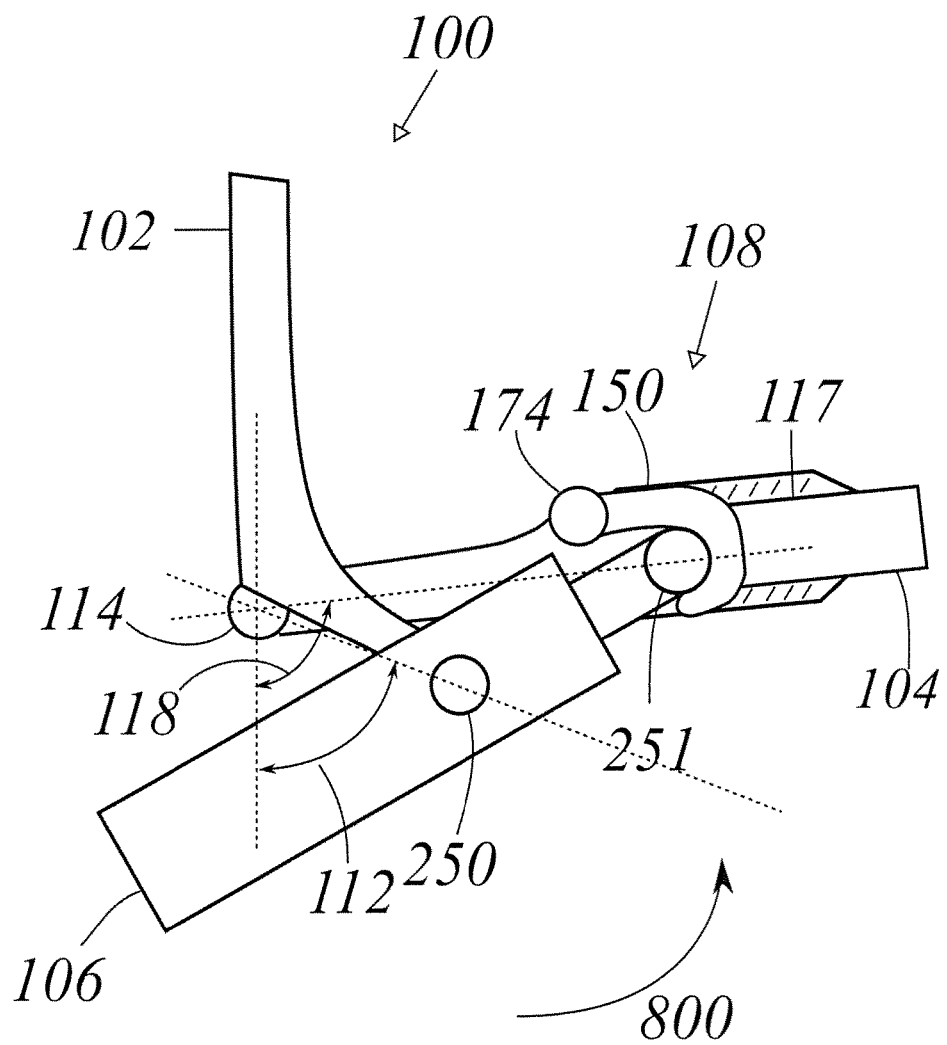
FIG. 5 shows an embodiment of the invention where a release mechanism 108 is in its first operational mode such that a force generator 106 provides a torque on a shank link 104 relative to a thigh link 102 along a direction 800.

In operation, when shank link 104 is flexing toward thigh link 102 (i.e. moving along arrow 800 as shown in FIG. 2) and the angle of shank link 104 relative to thigh link 102 (knee angle 118) is less than a predetermined toggle angle 112, release mechanism 108 is in its first operational mode. This means force generator 106 is becoming compressed, as shown in FIG. 2, and resists the flexing (flexion) of shank link 104 relative to thigh link 102. As shank link 104 flexes and moves toward thigh link 102 along direction 800, force generator 106 becomes compressed and shorter. Force generator 106 locks release mechanism 108 in its first operational mode and resists the flexion of shank link 104 relative to thigh link 102. When shank link 104 is flexing toward thigh link 102 along direction 800, the compressive force passes through knee joint 114 and produces no resistance torque at a toggle point. This is shown in FIG. 4. The angle between thigh link 102 and shank link 104 (knee angle 118) at this toggle point is the toggle angle 112. When shank link 104 continues to flex toward thigh link 102 and the angle of shank link 104 relative to thigh link 102 (knee angle 118) continues to grow larger than toggle angle 112 as shown in FIG. 5, release mechanism 108 is still in its first operational mode but the compressive force produces a torque that encourages the flexion of shank link 104 relative to thigh link 102.

Figure 6:
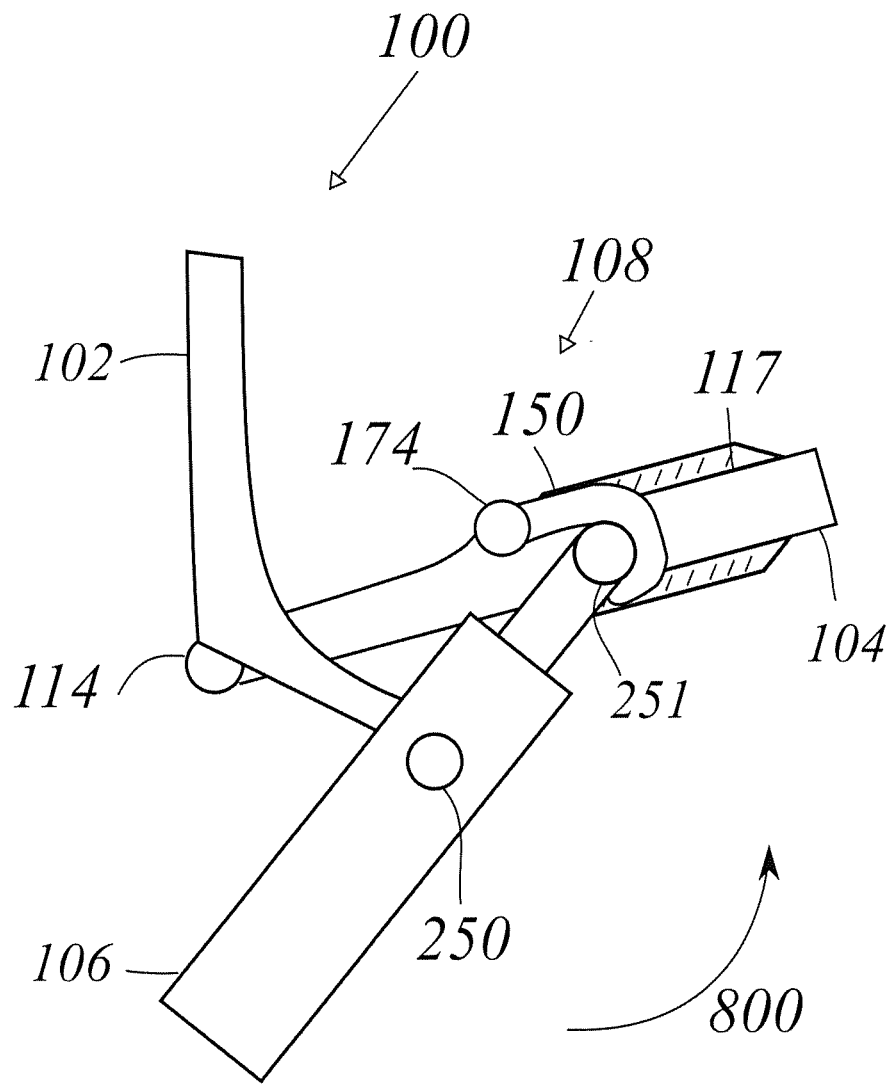
FIG. 6 shows an embodiment of the invention where release mechanism 108 is in its first operational mode such that force generator 106 reaches its natural length and the force of force generator is small or close to zero.
Figure 7:
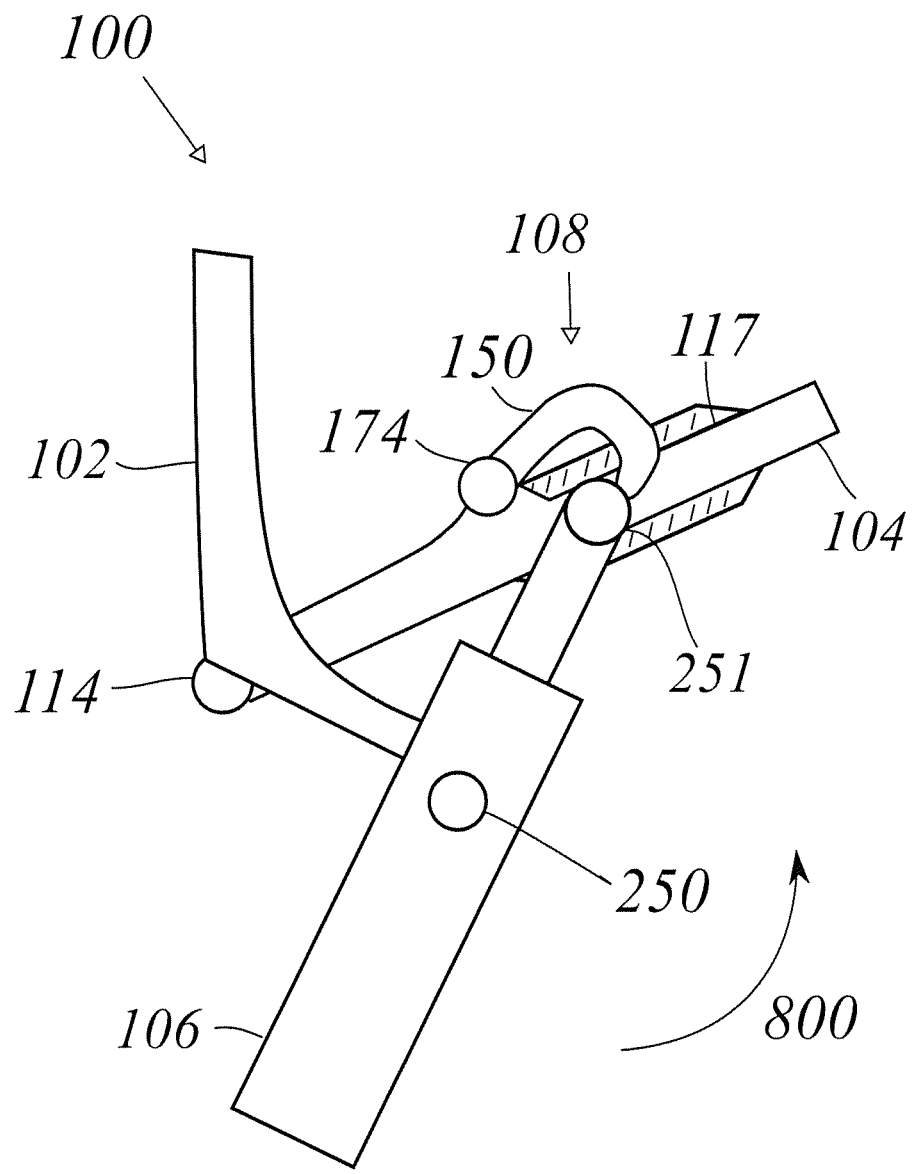
FIG. 7 shows an embodiment of the invention where release mechanism 108 is in its second operational mode such that force generator 106 does not provide any torque on shank link 104 relative to thigh link 102, when shank link 104 rotates relative to thigh link 102 along direction 800.

In other words, when shank link 104 moves along direction 800, as long as knee angle 118 is less than toggle angle 112, the compressive force of force generator 106 produces a moment that resists the flexion of shank link 104 relative to thigh link 102. At toggle angle 112, force generator 106 switches the direction of its produced torque. Once shank link 104 passes over the toggle point, force generator 106 starts to generate a torque which encourages the flexion of shank link 104. Force generator 106 eventually reaches its maximum natural length where the compressive force will be zero (FIG. 6). In this context, the term "maximum natural length" should be understood to mean an initial length of force generator 106 (e.g., length of rod 107 and cylinder 105) when a compression means (e.g., spring or air within cylinder 105) of the force generator 106 is not compressed or extended and force from the compression means is zero. At that time, where force generator 106 produces no force, release mechanism 108 moves to its second operational mode (FIG. 7). This means release mechanism 108 does not couple second end 251 of force generator 106 to shank link 104 and force generator 106 neither resists nor encourages the extension and flexion of shank link 104 from thigh link 102.

Figure 8:
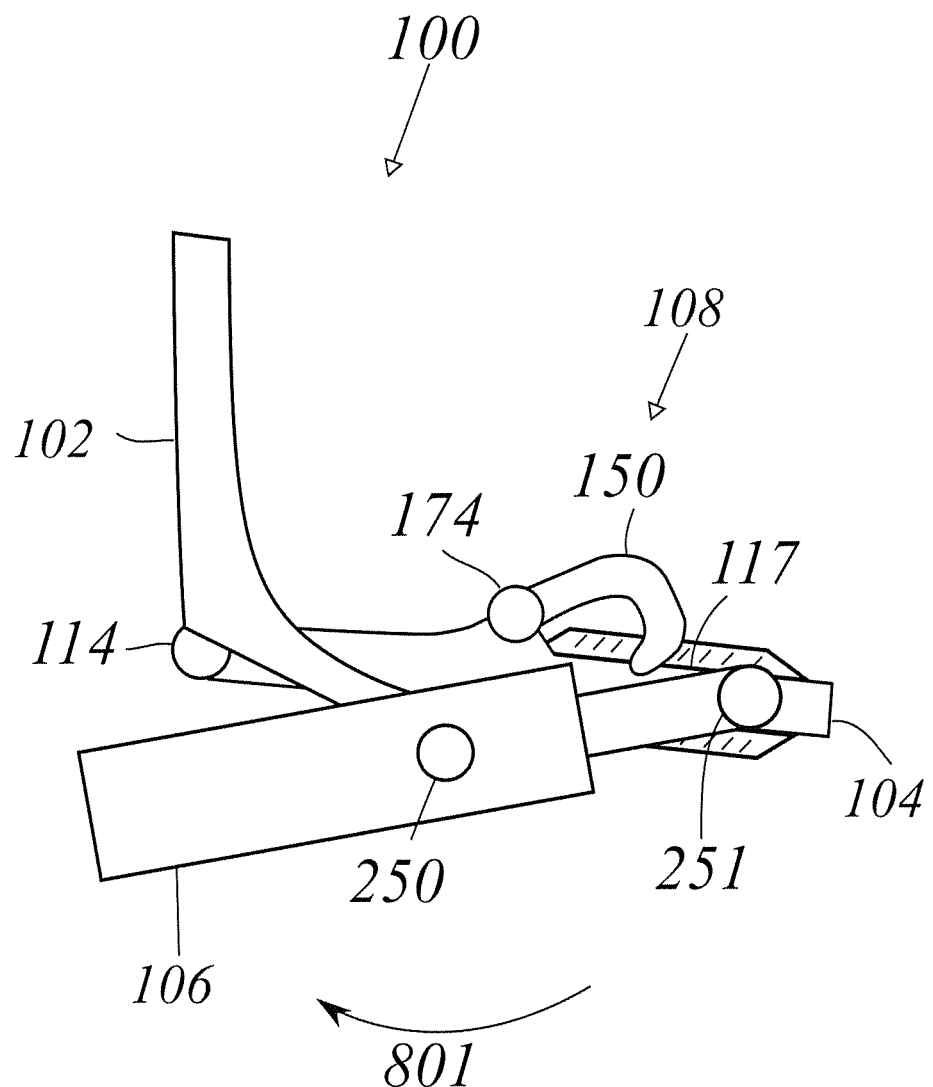
FIG. 8 shows an embodiment of the invention where release mechanism 108 is in its second operational mode such that force generator 106 does not provide any torque on shank link 104 relative to thigh link 102, when shank link 104 rotates relative to thigh link 102 along direction 801.
Figure 9:
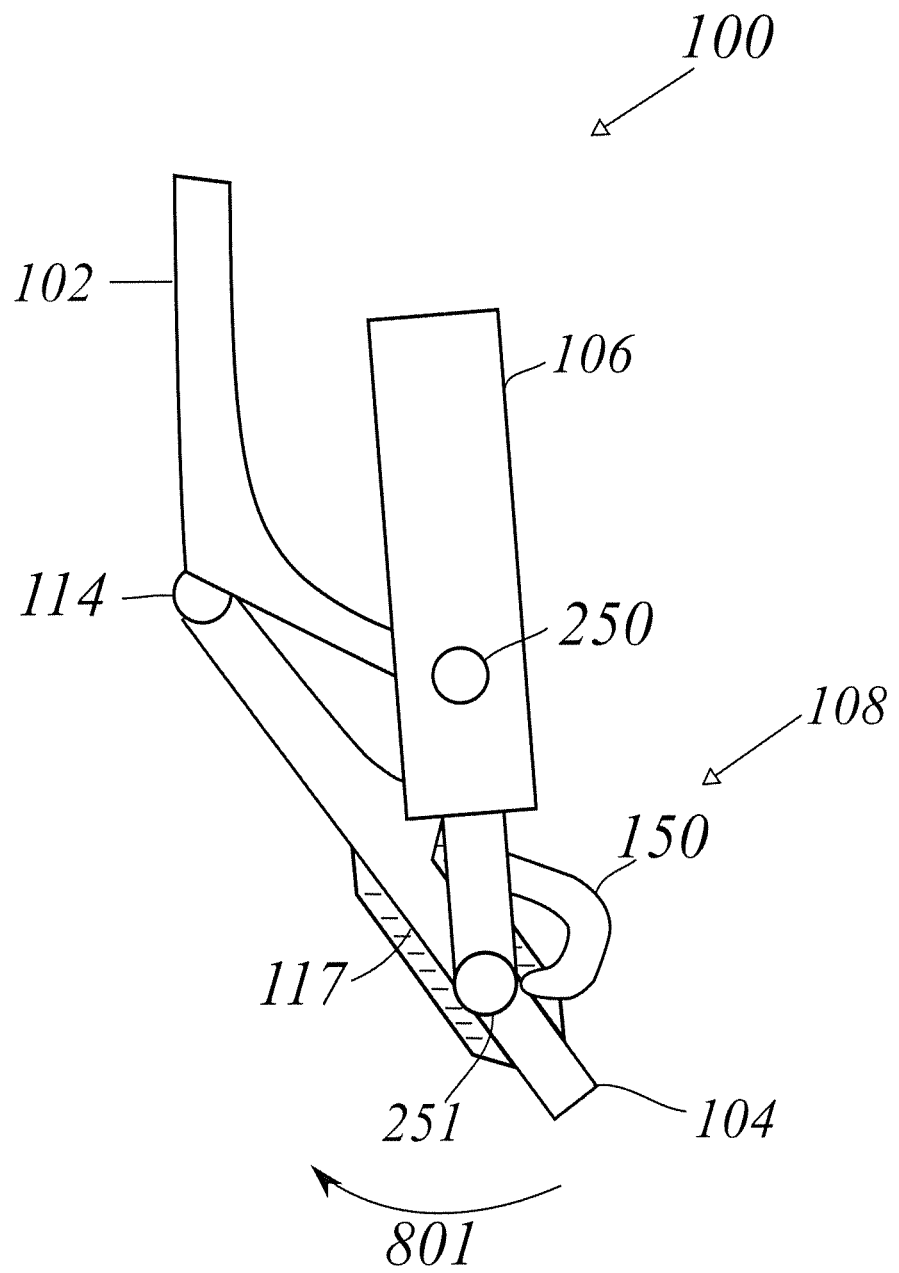
FIG. 9 shows FIG. 8 with a different angle of shank link 104 relative to thigh link 102.
Figure 10:
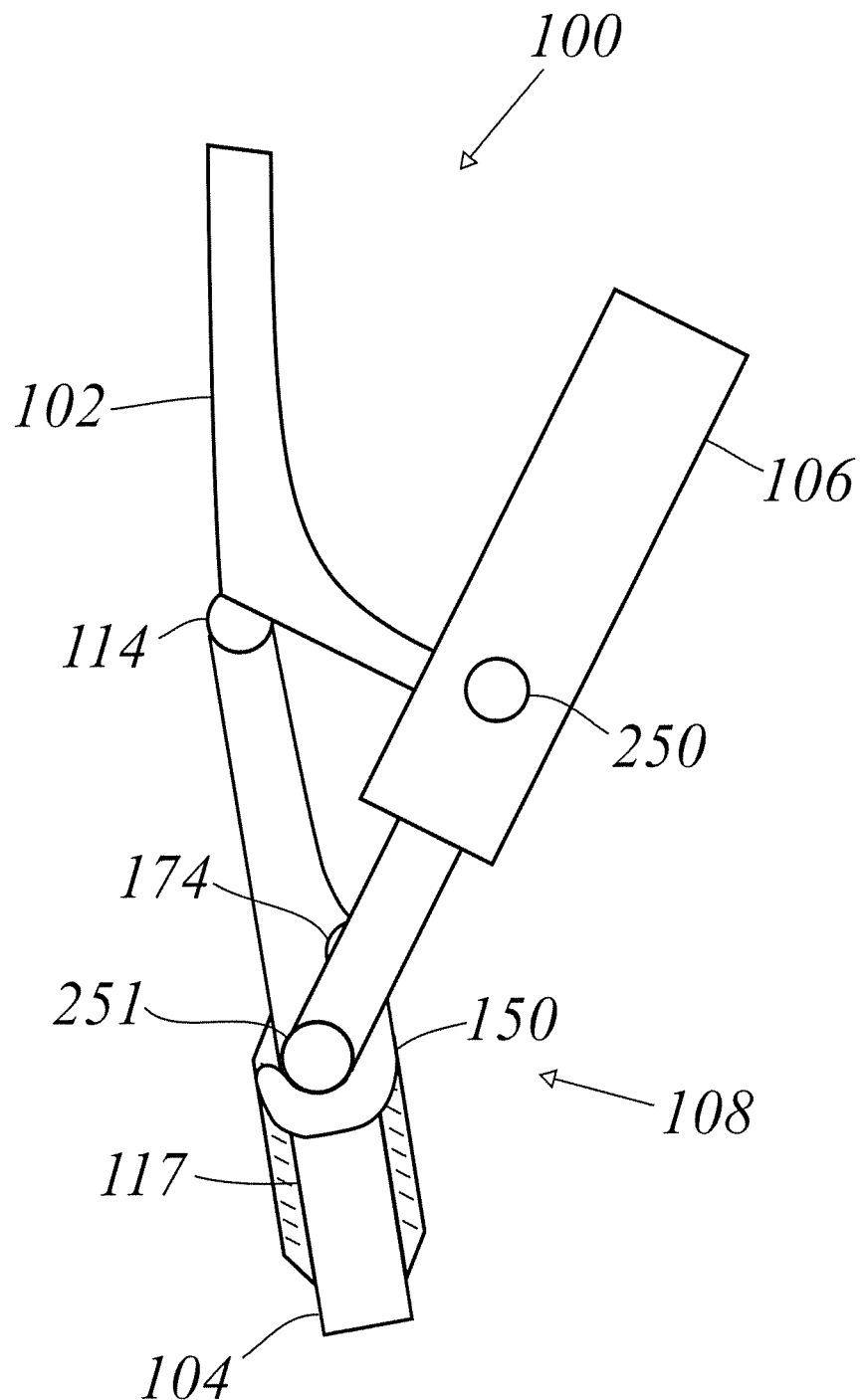
FIG. 10 shows an embodiment of the invention where release mechanism 108 moves into its first operational mode again from its second operational mode.

When shank link 104 is extending from thigh link 102 (i.e., is moving along direction 801 as in FIG. 8), release mechanism 108 remains in its second operational mode and force generator 106 is not engaged with shank link 104. In this mode, force generator 106 neither resists nor encourages the extension of shank link 104 from thigh link 102. This means shank link 104 extends freely relative to thigh link 102 along direction 801 as shown in FIGS. 8 and 9. When shank link 104 is sufficiently extended (e.g., 5 degree), the release mechanism 108 is able to move back to its first operational mode as shown in FIG. 10. This allows second end of force generator 106 to be coupled to shank link 104. As shank link 104 starts to flex again toward thigh link 102, the compressive force of force generator 106 locks release mechanism 108 in its first operational mode.

Figure 11:
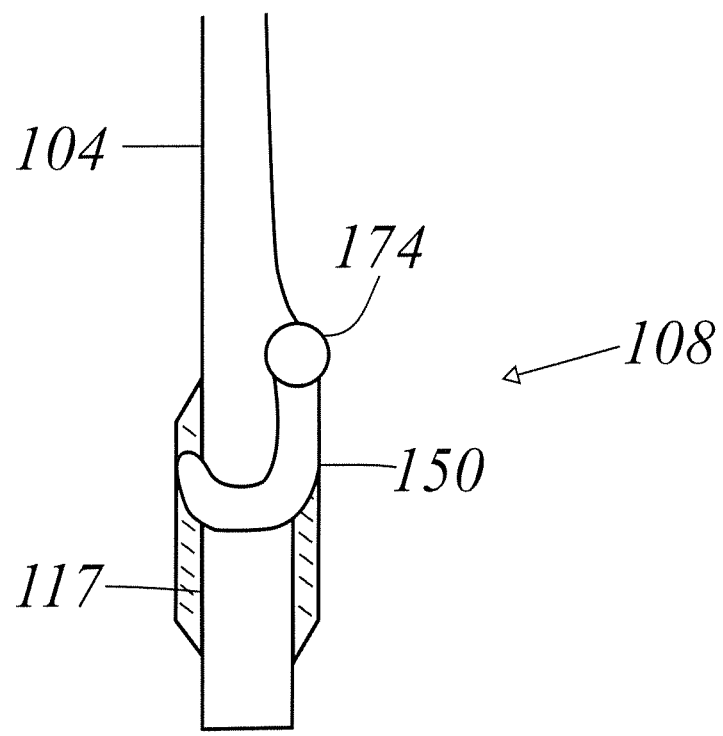
FIG. 11 shows an embodiment of a release mechanism 108 in one embodiment in its first operational mode where other parts have been removed for clarify.
Figure 12:
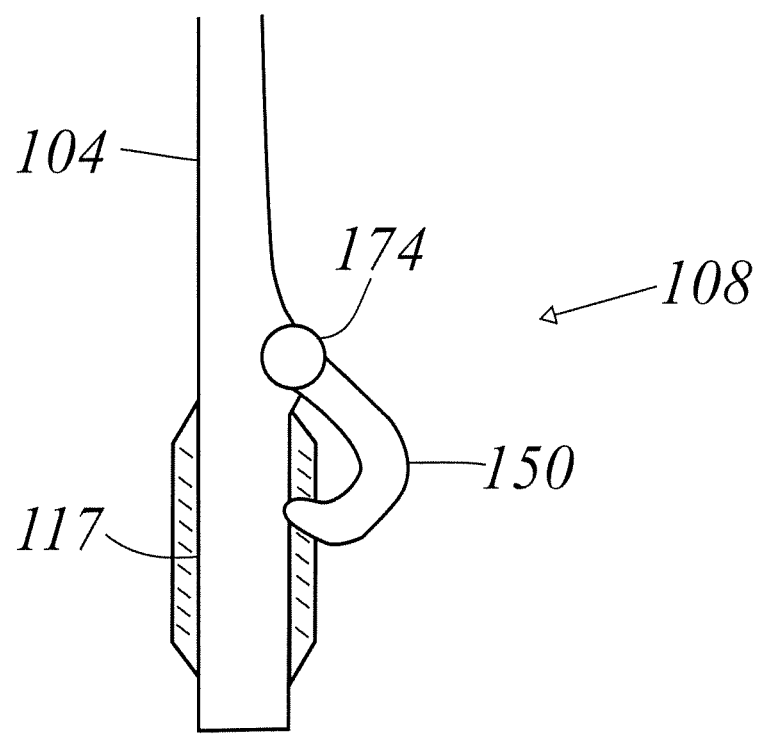
FIG. 12 shows an embodiment of a release mechanism 108 in one embodiment in its second operational mode where other parts have been removed for clarify.
Figure 13:
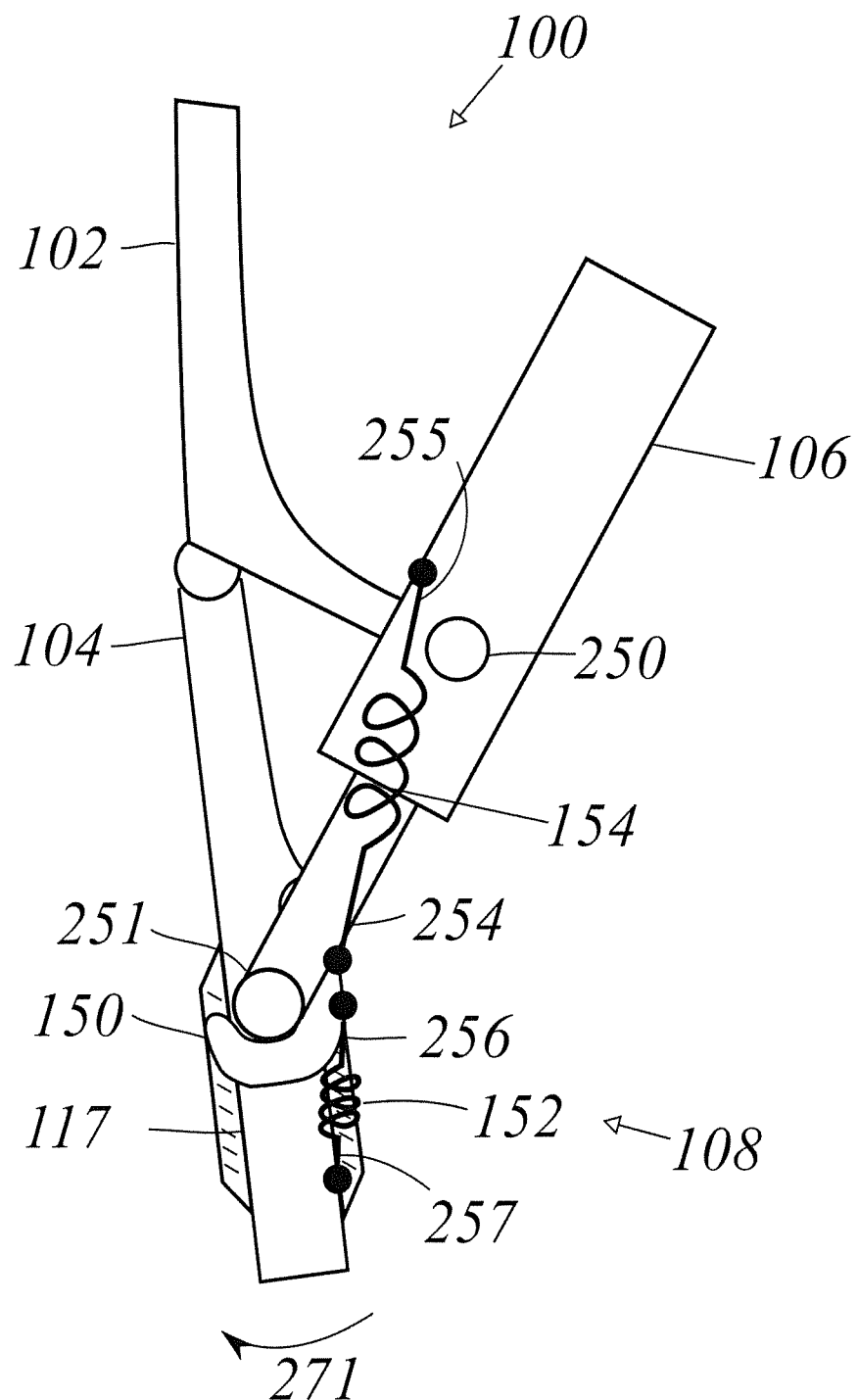
FIG. 13 shows release mechanism 108 in one embodiment in more detail when it is in its first operational mode.

FIGS. 11 and 12 shows a detailed schematic of an embodiment of the release mechanism 108 of FIG. 1. Release mechanism 108, comprises a hook 150, which is rotatably coupled to shank link 104 and rotates along a rotating point 174. Release mechanism 108 further comprises a constraint path 117 in shank link 104 allowing for motion of second end 251 of force generator 106. In some embodiments, constraint path 117 can be in the form of a slot formed in shank link 104, within which a portion of second end 251 is retained in a manner which enables it to slide within the slot. In some embodiments, constraint path 117 can be in the form of a track mounted to shank link 104, and a portion of second end 251 may be connected to the track in a manner that enables it to slide along a length of the track. One of ordinary skill in the art would understand that various configurations of constraint path could be utilized to constrain the motion of second end 251 of force generator 106 with respect to shank link 104, such that release mechanism 108 is able to couple to force generator 106 when release mechanism 108 is in its first operational mode. In other words, the second end 251 of force generator 106 is configured to move along constraint path 117 in or on shank link 104. Hook 150 is situated such that it is capable of blocking the motion of second end 251 of force generator 106 in/on constraint path 117 (e.g., the downward movement of second end 251 within constraint path 117 is blocked by hook 150). A trigger spring 154 is coupled to hook 150 from its first end 254 and, in embodiments, is coupled to force generator 106 from its second end 255, as shown in FIG. 13. One of ordinary skill in the art would understand that second end 255 of trigger spring 154 could be connected elsewhere (e.g., on thigh link 102) so long as, when shank link 104 flexes toward thigh link 102, the trigger spring 154 extends. A return spring 152 is coupled to hook 150 from its first end 256 and, in embodiments, to shank link 104 from its second end 257, as shown in FIG. 13. One of the ordinary skill in the art would understand that second end 257 of return spring 152, could be connected elsewhere (e.g., on shank link 104) so long as return spring 152 always pulls hook 150 toward constraint path (i.e., direction 271).

In operation, when release mechanism 108 is in its first operational mode (shown in FIG. 13), hook 150 is held stationary by the force of force generator 106. As shank link 104 flexes toward thigh link 102, trigger spring 154 is pulled by its second end 255, imposing a tensile force on hook 150. Trigger spring 154 stretches as shank link 104 flexes toward thigh link 102, however hook 150 is held stationary at its place by the force of force generator 106. As shown in FIG. 13, hook 150 has occupied constraint path 117; second end 251 of force generator 106 is blocked to move in constraint path 117, and the force of force generator 106 locks release mechanism 108 is in its first operational mode.

When force generator 106 is substantially extended to its natural length and compressive force of force generator 106 is substantially small or zero (FIG. 14), release mechanism 108 moves into its second operational mode. In the context of the present invention, "substantially small" means that the torque on the release mechanism 108 from the force of force generator 106 (friction force of second end 251 abutting force generator 106) plus the torque from the return spring 152, is smaller than the torque from a trigger spring trigger spring 154, such that the trigger spring is able to pull/push release mechanism 108 to move it to its second operational mode. When release mechanism 108 is in its second operational mode, hook 150 is moved by the force of trigger spring 154. Hook 150 is not blocking the motion of the second end 251 of force generator 106 within constraint path 117. This means when release mechanism 108 is in said second operational mode, force generator 106 neither resists nor encourages the extension and flexion of shank link 104 from said thigh link 102. In other words, when a force supplied by trigger spring 154 to hook 150 overcomes a force (friction force) supplied by force generator 106 plus a force supplied by return spring 152 to hook 150, then trigger spring 154 will pull hook 150 out of constraint path 117.

Figure 14:
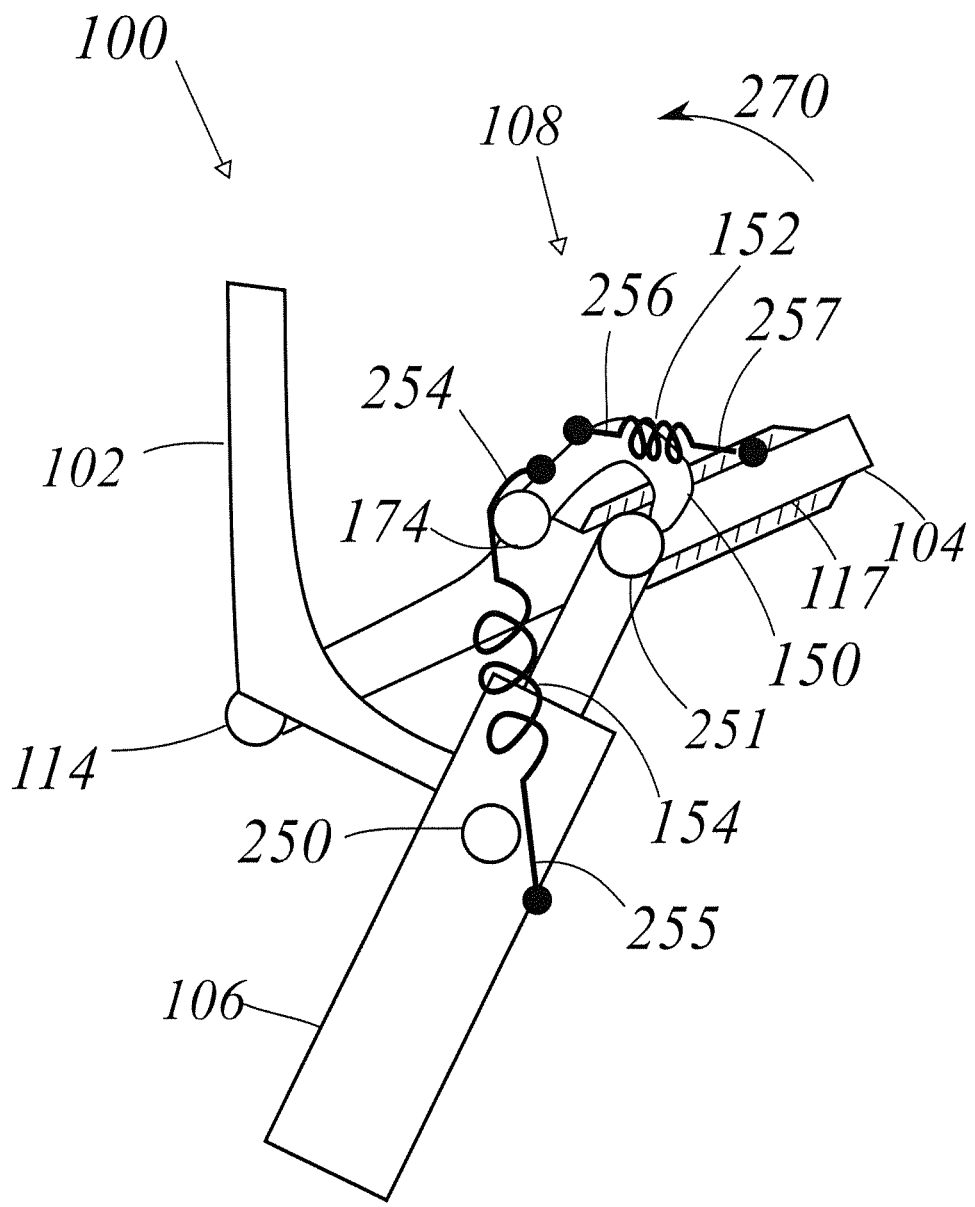
FIG. 14 shows release mechanism 108 in one embodiment in more detail when it is in its second operational mode.

As shown in FIG. 13, as shank link 104 starts to flex toward thigh link 102, first end 254 of trigger spring 154 is pulling hook 150. Hook 150 is blocking second end 251 of force generator 106. Release mechanism 108 moves into its first operational mode when force generator 106 holds hook 150 in its place. As shank link 104 flexes toward thigh link 102, trigger spring 154 stretches more. FIG. 14 shows the situation where the force of force generator 106 is zero or substantially small and hook 150 is rotated by trigger spring 154. Trigger spring 154 rotates hook 150 along direction 270 and switches release mechanism 108 to its second operational mode.

Figure 15:
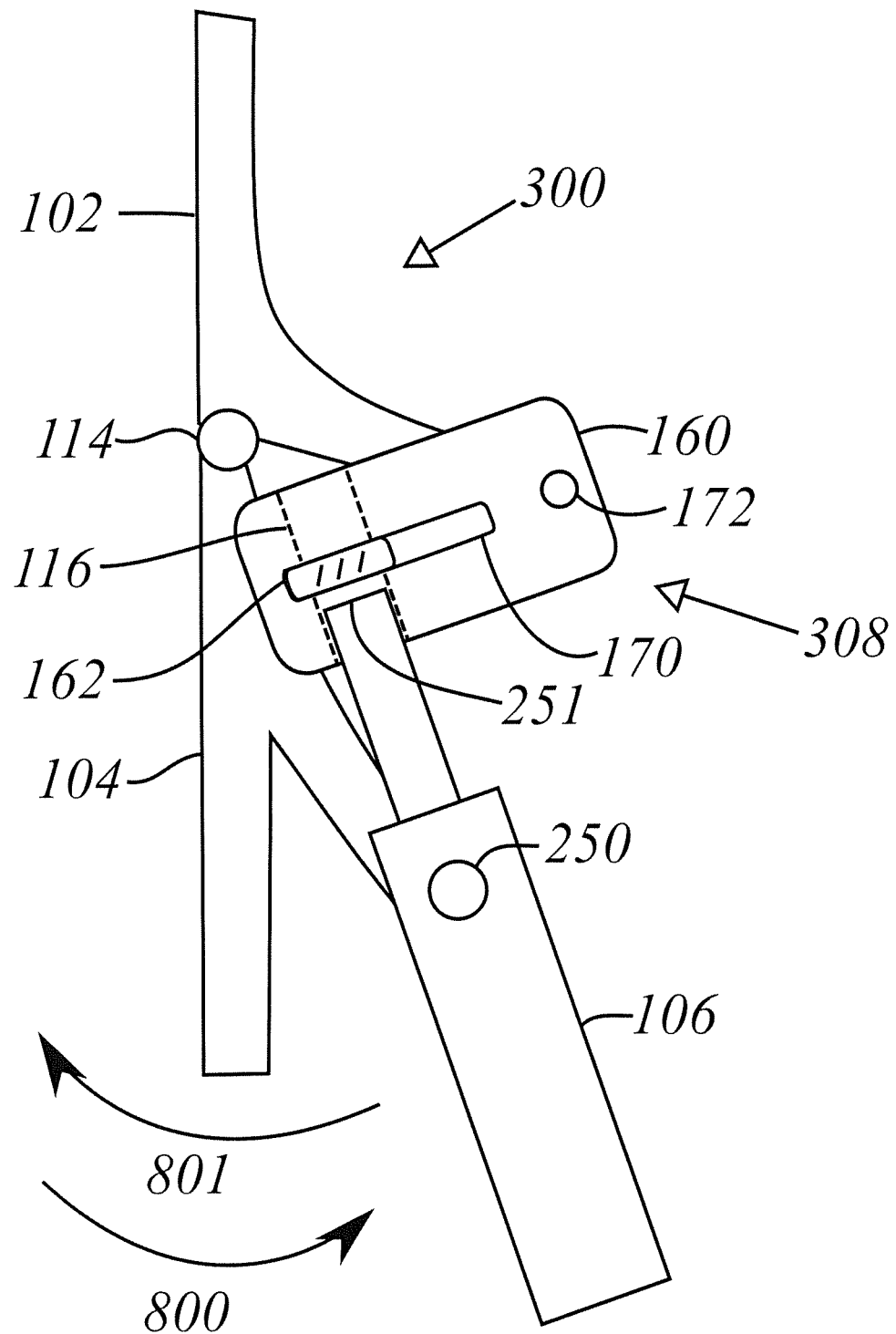
FIG. 15 shows another embodiment of the invention (second embodiment)

FIG. 15 shows a second embodiment of passive power-conservative artificial knee 300 shown again without person 200 for clarity. Passive power-conservative artificial knee 300, among other things, comprises a thigh link 102, a shank link 104, a compressive force generator 106, and a release mechanism 308. Shank link 104 is rotatably coupled to thigh link 102 along knee joint 114.

In the embodiment of FIG. 15, passive compressive force generator 106 is rotatably coupled to shank link 104 from its first attachment end 250. Force generator 106 is capable of generating a compressive force between its first attachment end 250 and its second attachment end 251 (hereinafter ends 250, 251). Both ends 250, 251 of force generator 106 resist to move toward each other when both ends 250 and 251 are pushed toward to each other. The resistance force that tries to keep first end 250 and second end 251 away from each other is called compressive force. In some embodiments of the invention, the passive compressive force generator of the second embodiment is a gas spring as shown in FIG. 15. In some embodiments of the invention, the passive compressive force generator of the second embodiment is an air spring. In some embodiments of the invention, the passive compressive force generator of the second embodiment is a compression coil spring. A common characteristic among all embodiments of passive compressive force generators is that both ends of force generator 106 resist movement of ends 250 and 251 toward each other, such as when both ends 250 and 251 are pushed toward to each other.

In the embodiment of FIG. 15, a release mechanism 308 is coupled to thigh link 102. Release mechanism 308 has at least two operational modes. In its first operational mode, release mechanism 308 rotatably couples second end 251 of force generator 106 to thigh link 102. This means release mechanism 308 allows the compressive force to be imposed on thigh link 102. In its second operational mode, release mechanism 308 does not couple second end 251 of force generator 106 to thigh link 102. This means release mechanism 308, in this second operational mode, does not allow the compressive force of force generator 106 to be imposed on thigh link 102. Release mechanism 308 is described below.

Figure 16:
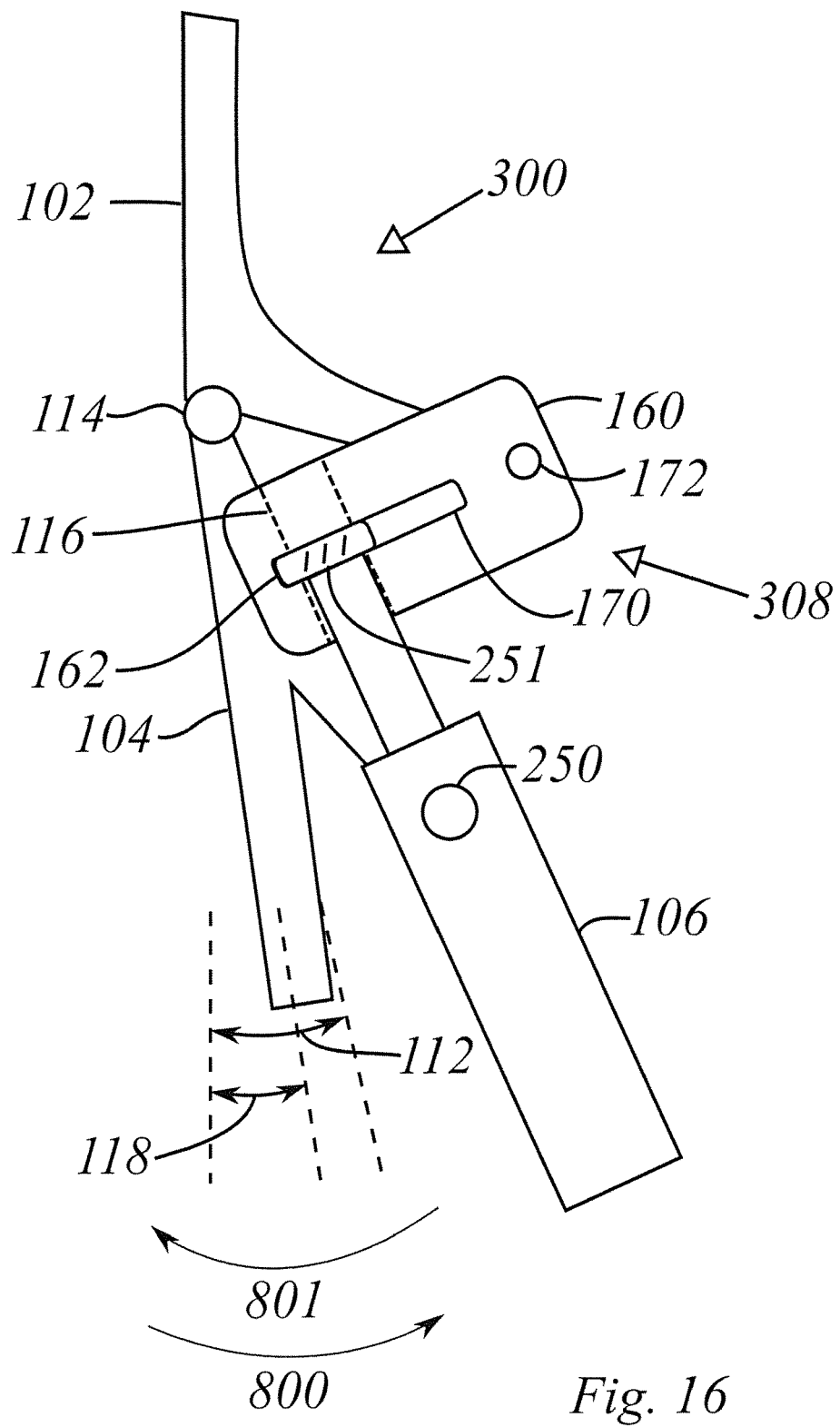
FIG. 16 depicts the second embodiment of the invention where release mechanism 308 is in its first operational mode such that force generator 106 provides a torque on shank link 104 relative to thigh link 102 along direction 801.
Figure 18:
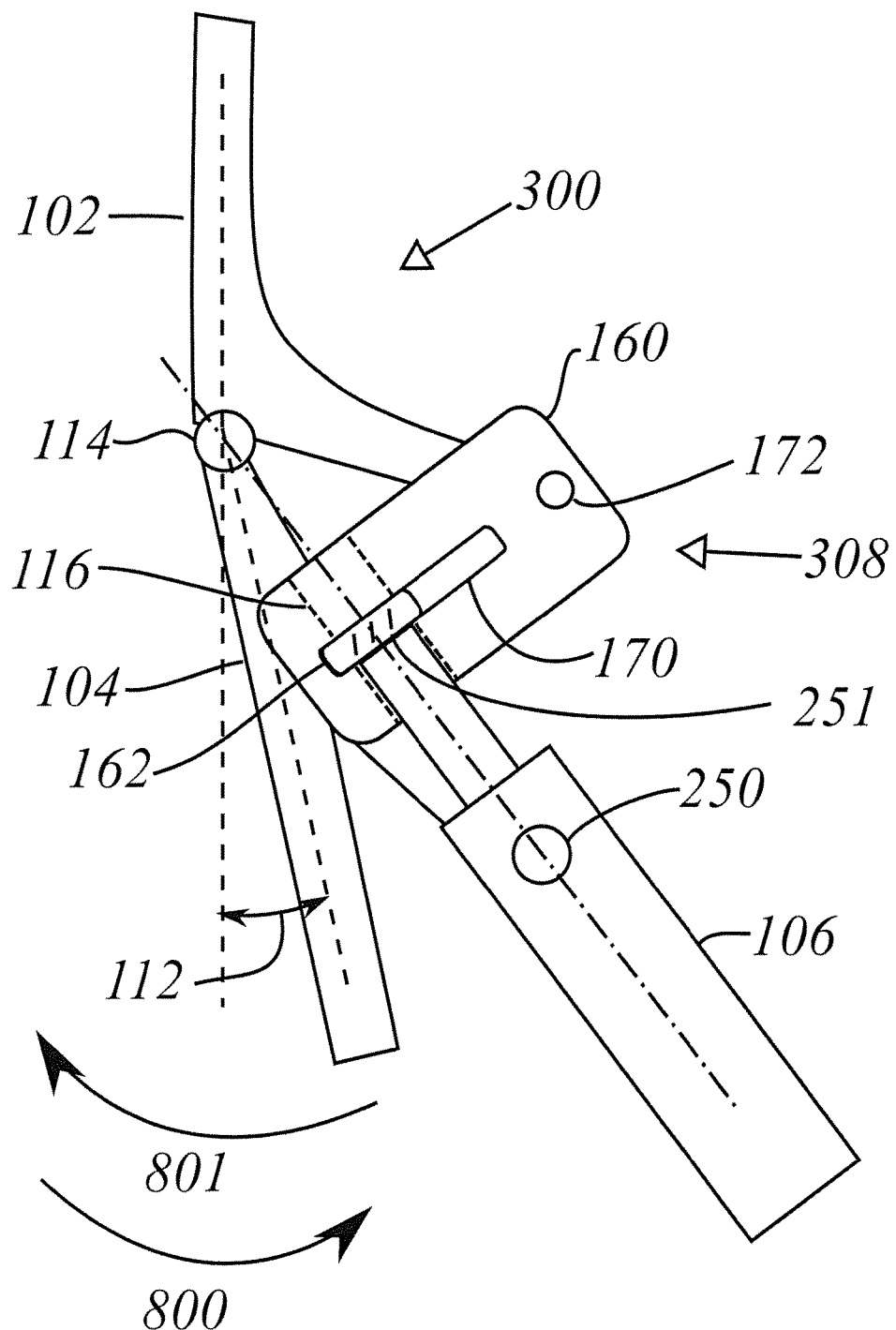
FIG. 18 shows the second embodiment of the invention where the angle of shank link 104 relative to thigh link 102 is equal to a toggle angle 112 such that force generator 106 does not provide torque on shank link 104 relative to thigh link 102.
Figure 19:
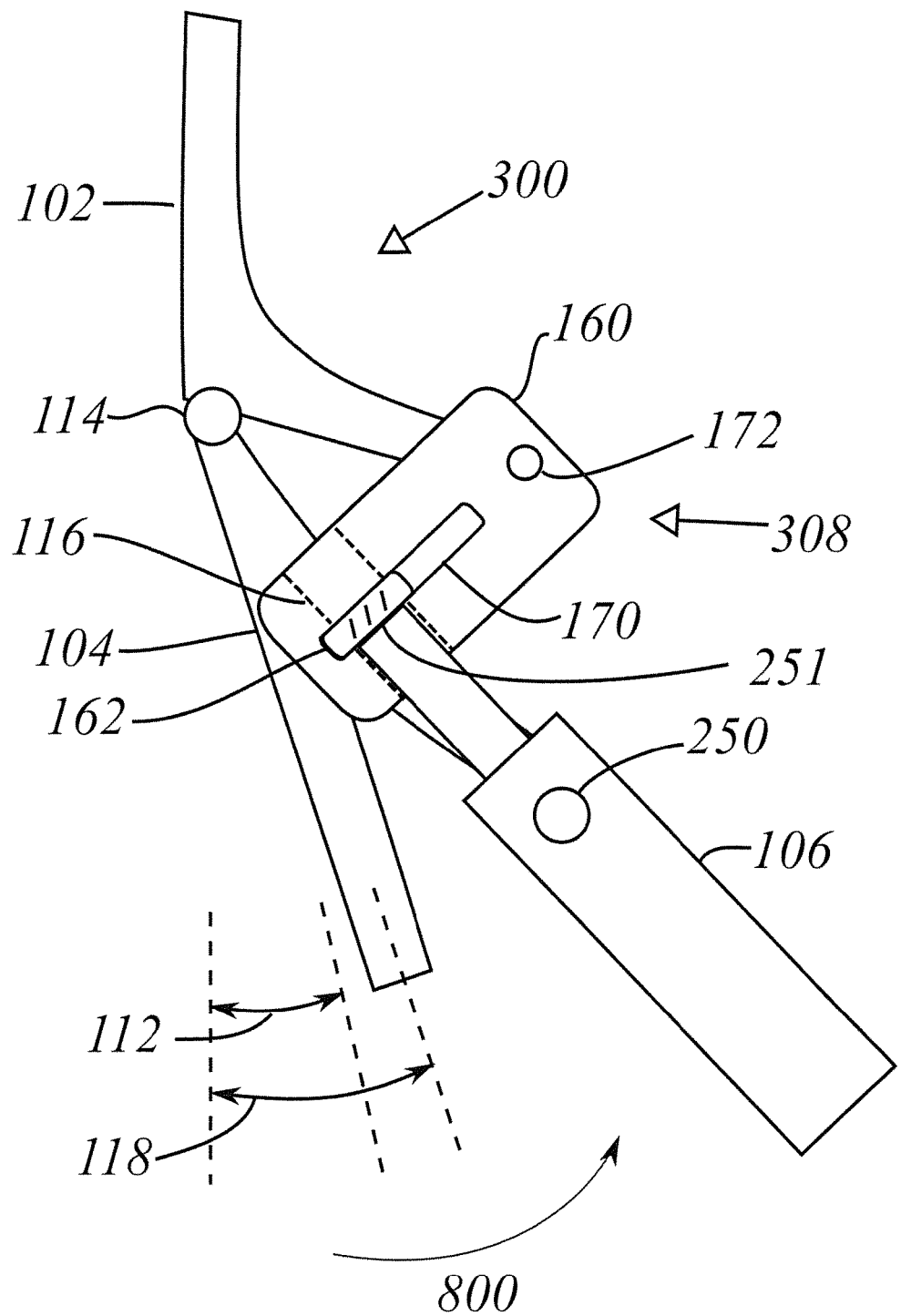
FIG. 19 shows the second embodiment of the invention where release mechanism 308 is in its first operational mode such that force generator 106 provides a torque on shank link 104 relative to thigh link 102 along direction 800.

In operation, when shank link 104 is flexing toward thigh link 102 (i.e. moving along direction 800 as shown in FIG. 16) and the angle of shank link 104 relative to thigh link 102 is less than a predetermined toggle angle 112, release mechanism 308 is in its first operational mode. This means force generator 106 is becoming compressed, as shown in FIG. 16, and resists the flexion of shank link 104 relative to thigh link 102. As shank link 104 flexes and moves toward thigh link 102 along direction 800, force generator 106 becomes compressed and shorter. Force generator 106 locks release mechanism 308 in its first operational mode and resists the flexion of shank link 104 relative to thigh link 102. When shank link 104 is flexing toward thigh link 102, the compressive force passes through knee joint 114 and produces no resistance torque at a toggle point. This is shown in FIG. 18. The angle between thigh link 102 and shank link 104 at this toggle point is called the toggle angle 112. When shank link 104 continues to flex toward thigh link 102 and the angle of shank link 104 relative to thigh link 102 continues to grow larger than toggle angle 112 as shown in FIG. 19, release mechanism 308 is still in its first operational mode but the compressive force produces a torque that encourages the flexion of shank link 104 relative to thigh link 102.

Figure 20:
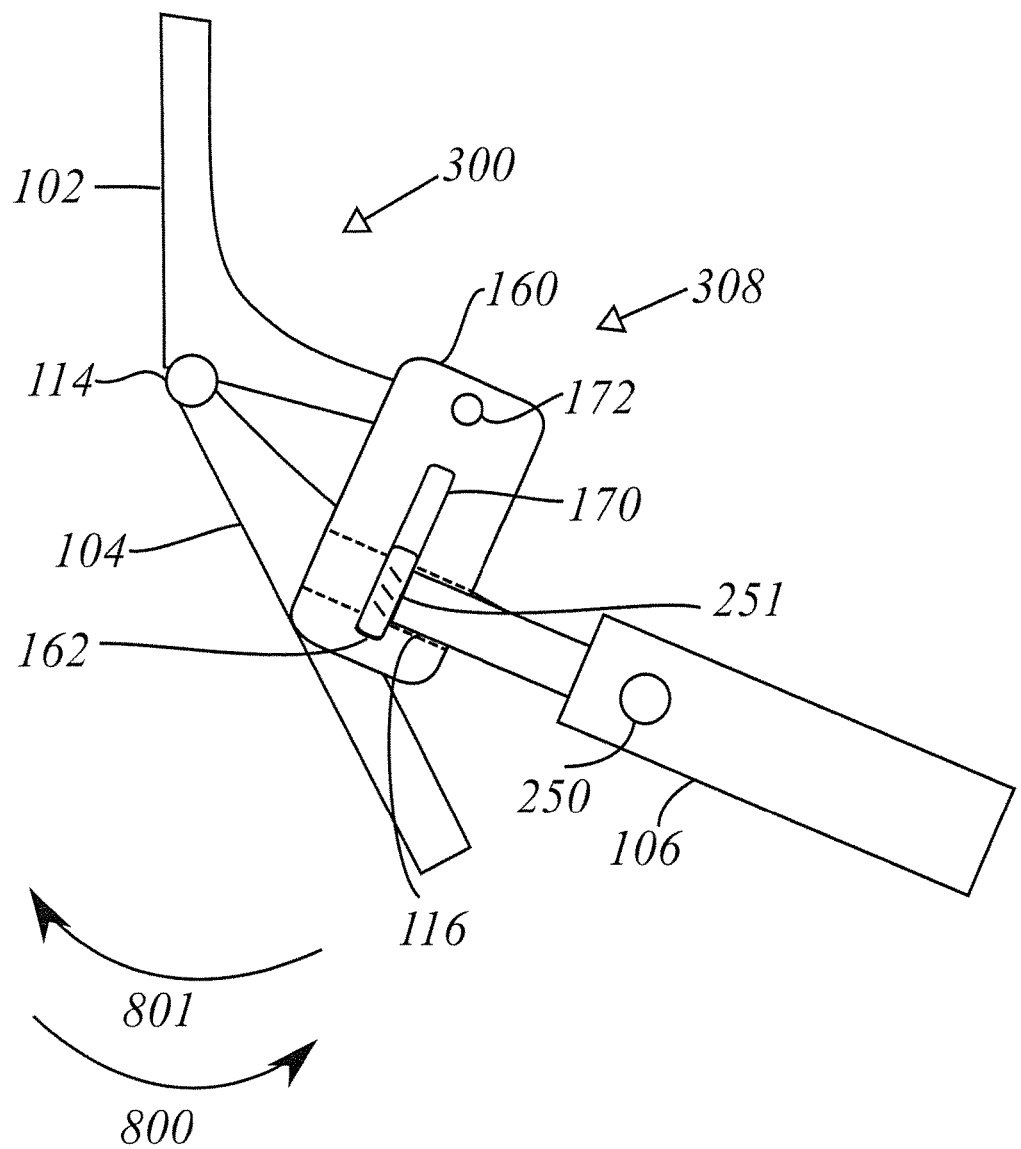
FIG. 20 shows the second embodiment of the invention where release mechanism 308 is in its first operational mode such that force generator 106 reaches its natural length and the force of force generator 106 is small or close to zero.
Figure 21:
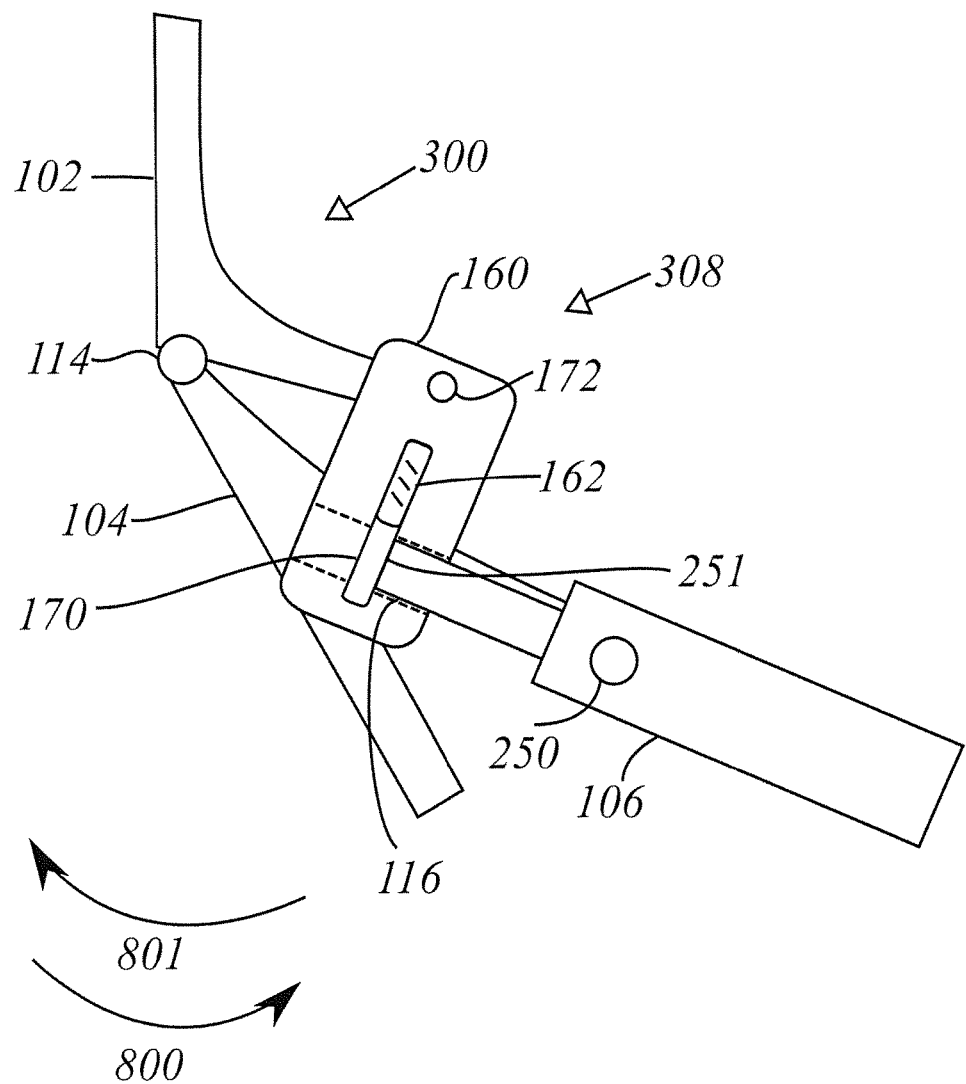
FIG. 21 shows the second embodiment of the invention where release mechanism 308 is in its second operational mode such that force generator 106 does not provide any torque on shank link 104 relative to thigh link 102, when shank link 104 rotates relative to thigh link 102 along direction 800.

In other words, when shank link 104 moves along direction 800, as long as the angle between shank link 104 and thigh link 102 is less than toggle angle 112, the compressive force of force generator 106 produces a moment that resists the flexion of shank link 104 relative to thigh link 102. At toggle angle 112, force generator 106 switches the direction of its produced torque. Once shank link 104 passes over the toggle point, force generator 106 starts to generate a torque which encourages the flexion of shank link 104. Force generator 106 eventually reaches its maximum natural length where the compressive force will be zero (FIG. 20). At that time where force generator 106 produces no force, release mechanism 308 moves to its second operational mode (FIG. 21). This means release mechanism 308 does not couple second end 251 of force generator 106 to thigh link 102 and force generator 106 neither resists nor encourages the extension and flexion of shank link 104 from thigh link 102.

Figure 22:
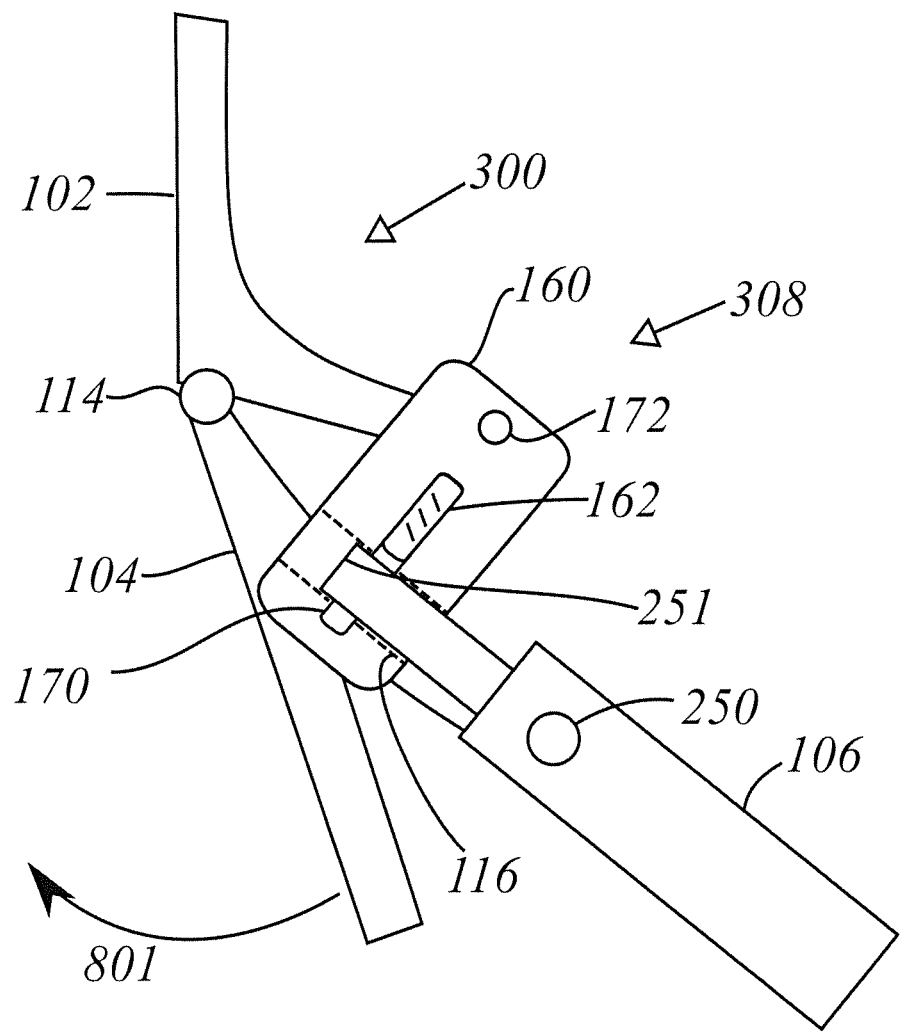
FIG. 22 shows the second embodiment of the invention where release mechanism 308 is in its second operational mode such that force generator 106 does not provide any torque on shank link 104 relative to thigh link 102, when shank link 104 rotates relative to thigh link 102 along direction 801.
Figure 23:
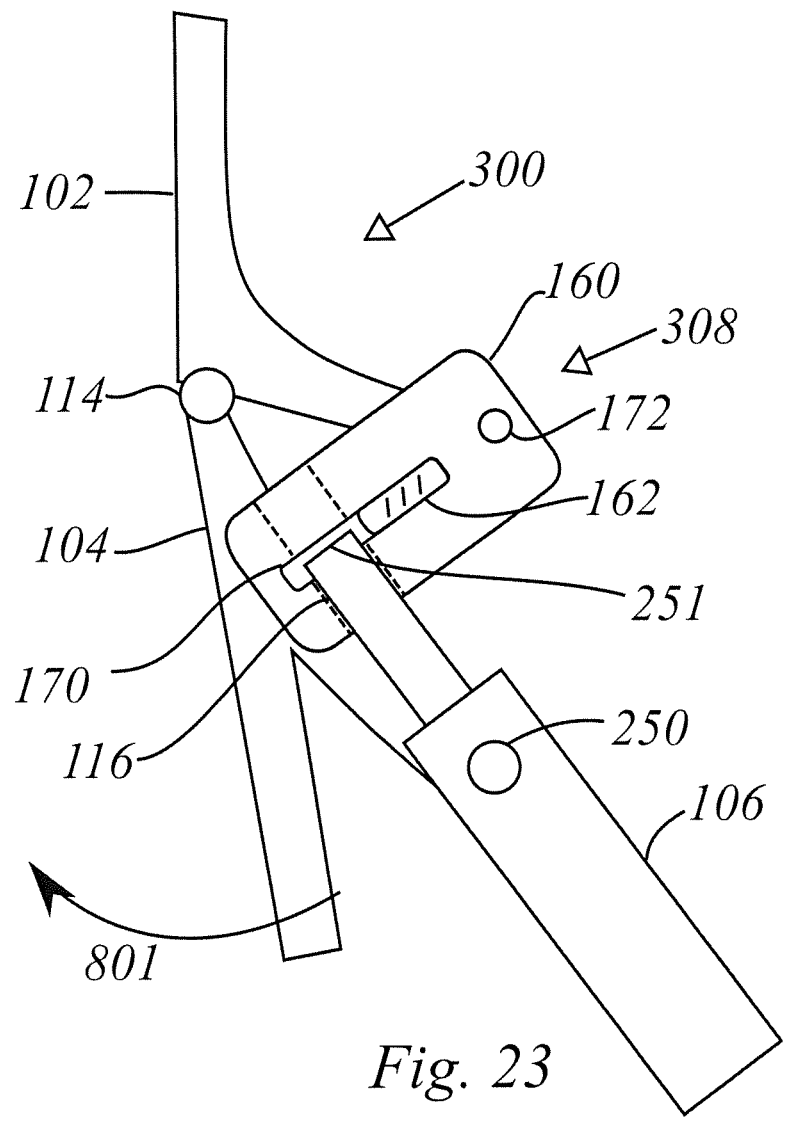
FIG. 23 shows FIG. 22 with a different angle of shank link 104 relative to thigh link 102 in the second embodiment.
Figure 24:
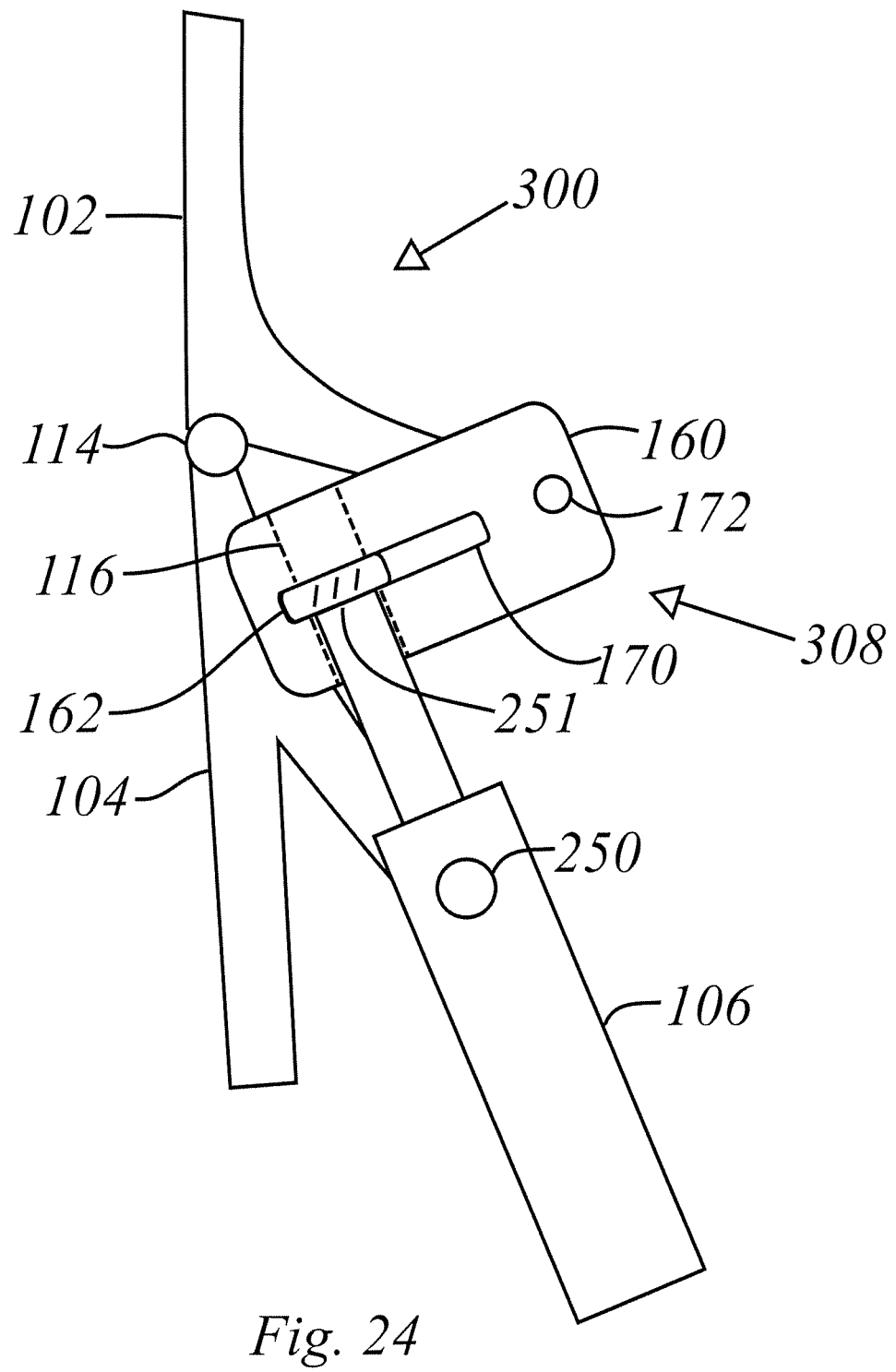
FIG. 24 shows the second embodiment of the invention where release mechanism 308 moves into its first operational mode again from its second operational mode.

When shank link 104 is extending from thigh link 102 (i.e. is moving along direction 801 as in FIG. 22), release mechanism 308 remains in its second operational mode and force generator 106 is not engaged with thigh link 102. In this mode, force generator 106 neither resists nor encourages the extension of shank link 104 from thigh link 102. This means shank link 104 extends freely relative to thigh link 102 along direction 801 as shown in FIGS. 22 and 23. When shank link 104 reaches its maximum extension location as shown in FIG. 24, release mechanism 308 moves into its first operational mode and couples end of force generator 106 to thigh link 102. As shank link 104 starts to flex toward thigh link 102, the compressive force of force generator 106 locks release mechanism 308 in its first operational mode.

Figure 25:
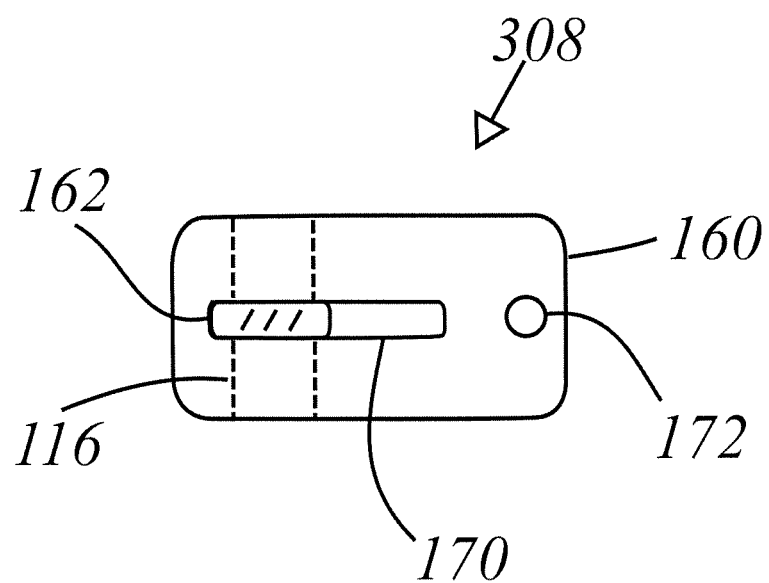
FIG. 25 shows the second embodiment of a release mechanism 308 in its first operational mode where other parts have been removed for clarify.
Figure 27:
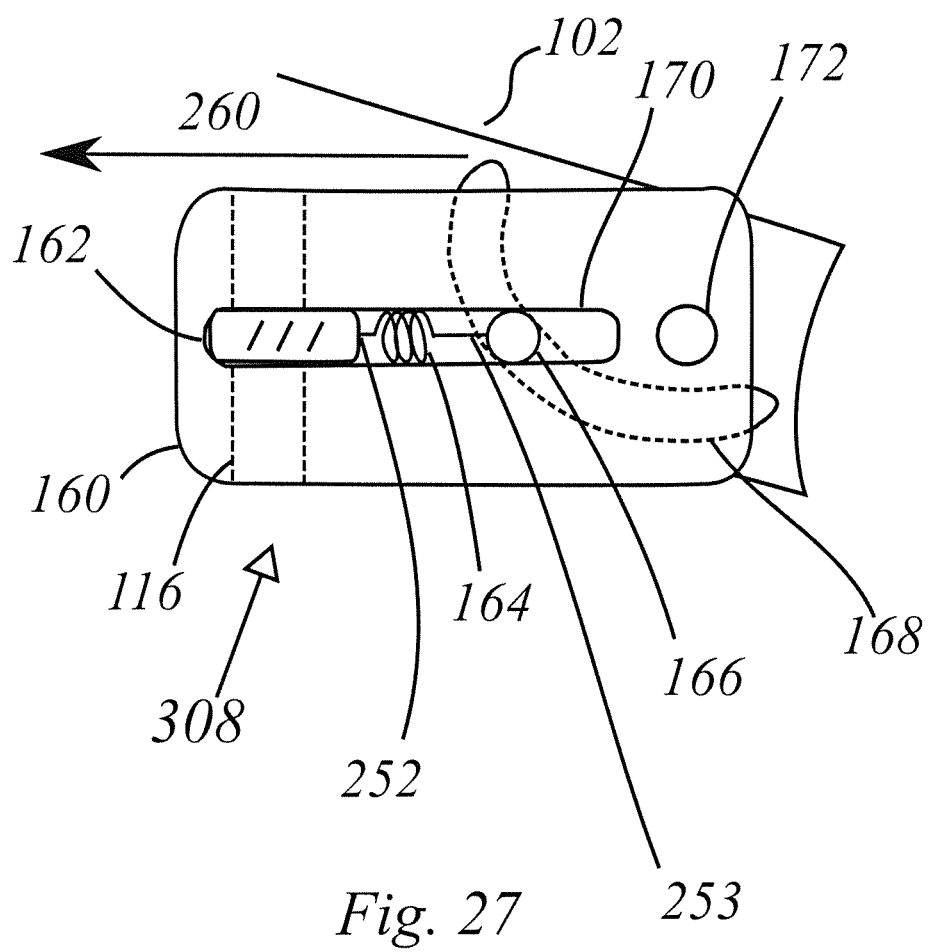
FIG. 27 shows release mechanism 308 in the second embodiment in more detail when it is in its first operational mode.
Figure 29:
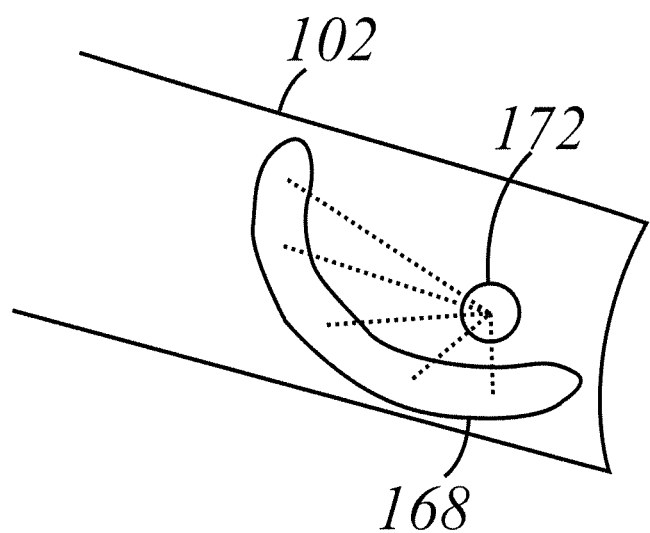
FIG. 29 shows how cam slot 168 has different radii in different angles along rotating point 172.

FIG. 27 shows a detailed schematic of an embodiment of release mechanism 308. Release mechanism 308 of FIG. 27 comprises a holding block 160, which is rotatably coupled to thigh link 102 and rotates along a rotating point 172. Release mechanism 308 further comprises a constraint path 116 within holding block 160 and defined by portions of a body of holding block 160, allowing for motion of second end 251 of said force generator 106 within holding block 160. In other words, the second end 251 of force generator 106 can move along constraint path 116 in holding block 160. Release mechanism 308 additionally comprises a moving block 162 that moves in a release slot 170 within holding block 160 and defined by portions of the body of holding block 160. Release slot 170 is situated such that moving block 162 is capable of blocking the motion of second end 251 of force generator 106 within constraint path 116. A trigger spring 164 is coupled to moving block 162 from its first end 252 and to a guiding piece 166 from its second end 253. Release mechanism 308 further comprises a guiding piece 166 coupled to second end 253 of trigger spring 164. Guiding piece 166 moves in a cam slot 168 on thigh link 102. Trigger spring 164 connects guiding piece 166 and moving block 162 together. Cam slot 168 has different radii in different angles along rotating point 172 as shown in FIG. 29. In operation when release mechanism 308 is in its first operational mode (shown in FIGS. 25 and 27), moving block 162 is held stationary in release slot 170 by the force of force generator 106. As shank link 104 flexes toward thigh link 102, trigger spring 164 is pulled by its second end 253 imposing a tensile force on moving block 162. Trigger spring 164 stretches as shank link 104 flexes toward thigh link 102, however moving block 162 is held stationary at its place by the force of force generator 106. As shown in FIG. 27, moving block 162 has occupied constraint path 116; second end 251 of force generator 106 is blocked to move in constraint path 116 and the force of force generator 106 locks release mechanism 308 is in its first operational mode.

Figure 26:
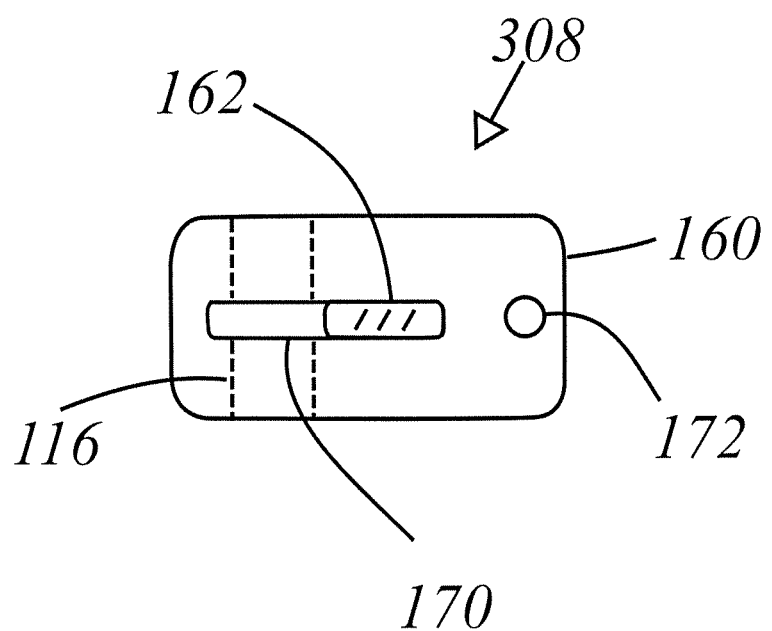
FIG. 26 shows the second embodiment of a release mechanism 308 in its second operational mode where other parts have been removed for clarify.

When force generator 106 is substantially extended to its natural length and compressive force of force generator 106 is substantially small or zero (e.g. when knee angle 118 is 55 degree) (FIGS. 26 and 28), release mechanism 308 moves into its second operational mode. In the context of the present invention, "substantially small" means that the torque on the release mechanism 308 from the force of force generator 106 (friction force of second end 251 abutting moving block 162 of force generator 106) is smaller than the torque from a trigger spring 164, such that the trigger spring 164 is able to pull release mechanism 308 to move it to its second operational mode. When release mechanism 308 is in its second operational mode, moving block 162 and trigger spring 164 move due to the motion of shank link 104 relative to thigh link 102. Moving block 162 is not blocking the motion of the second end 251 of force generator 106. This means when release mechanism 308 is in said second operational mode, force generator 106 neither resists nor encourages the extension and flexion of shank link 104 from said thigh link 102.

As shown in FIG. 27, as shank link 104 starts to flex toward thigh link 102, guiding piece 166 and moving block 162 are pushed toward direction 260. Moving block 162 is blocking second end 251 of force generator 106. Release mechanism 308 moves into its first operational mode when force generator 106 holds moving block 162 in its place. As shank link 104 flexes toward thigh link 102, guiding piece 166 gets closer to rotating point 172 and stretches trigger spring 164.

Figure 28:
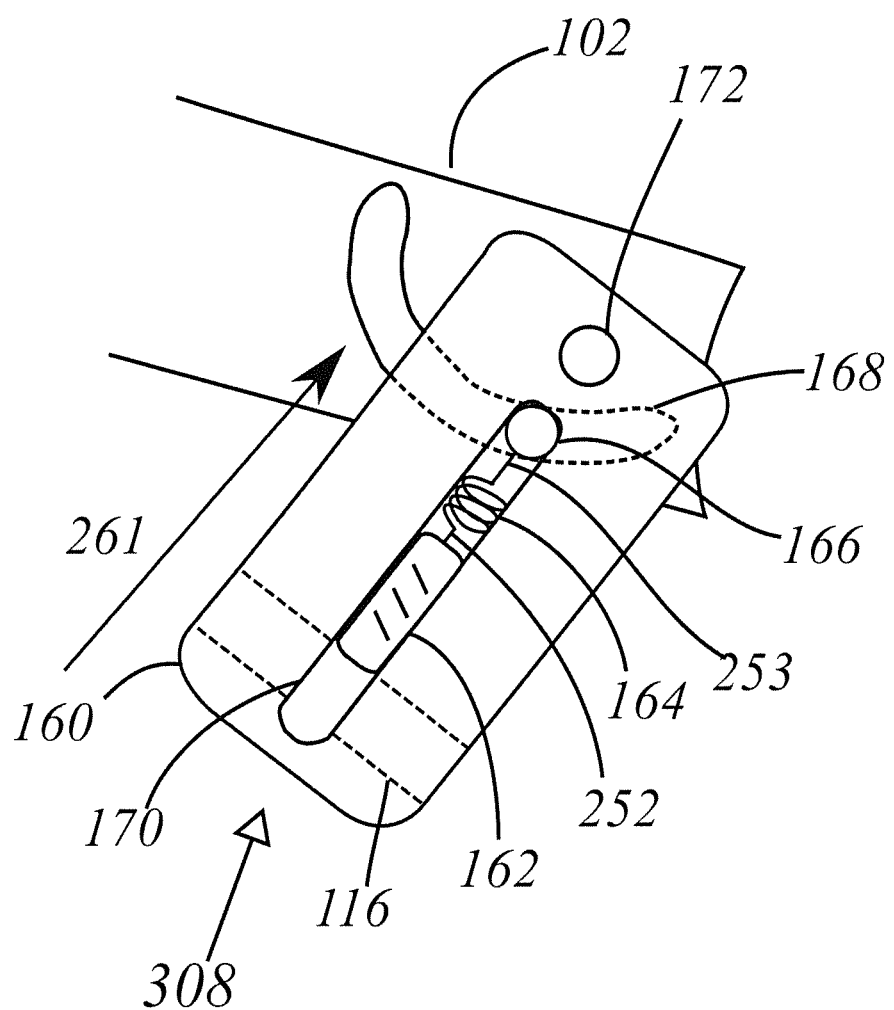
FIG. 28 shows release mechanism 308 in the second embodiment in more detail when it is in its second operational mode.
Figure 33:
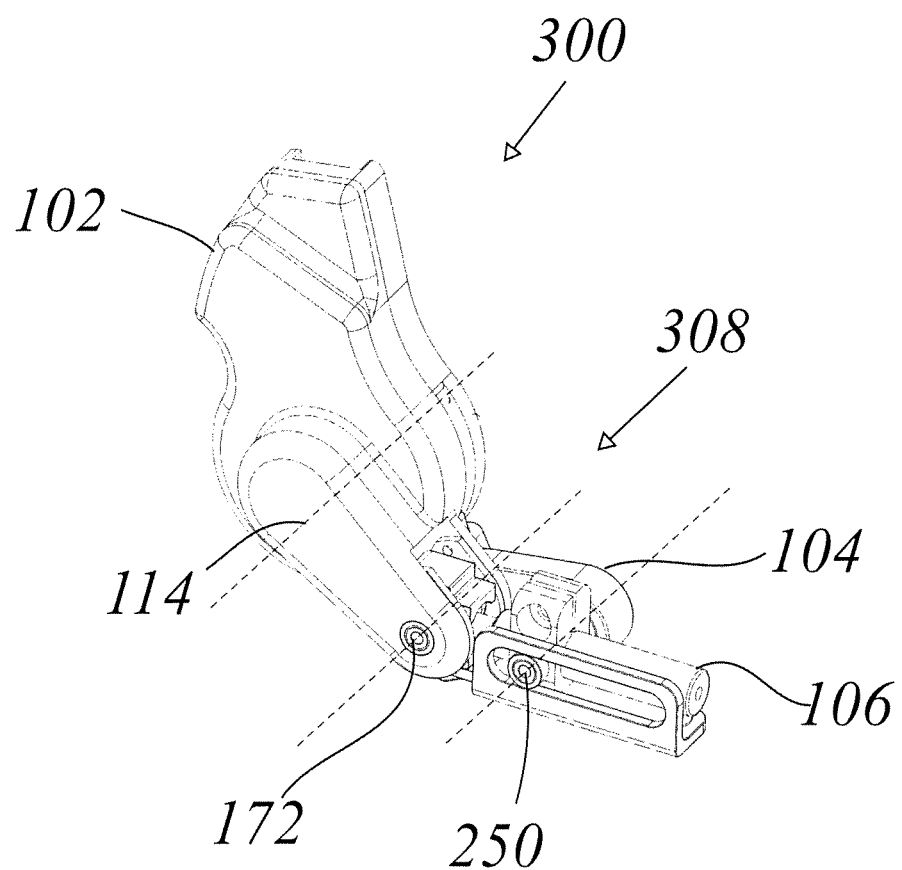
FIG. 33 shows the second embodiment in practice.

FIG. 28 shows the situation where the force (friction force) of force generator 106 on moving block 162 is zero or substantially small and moving block 162 is released. Trigger spring 164 pulls moving block 162 toward direction 261 and switches release mechanism 308 to its second operational mode. In other words, when a force supplied by trigger spring 164 to moving block 162 overcomes a force supplied by force generator 106 to moving block 162, then trigger spring 164 will pull moving block 162 out of constraint path 116. FIG. 33 shows an embodiment in practice.

Figure 30:
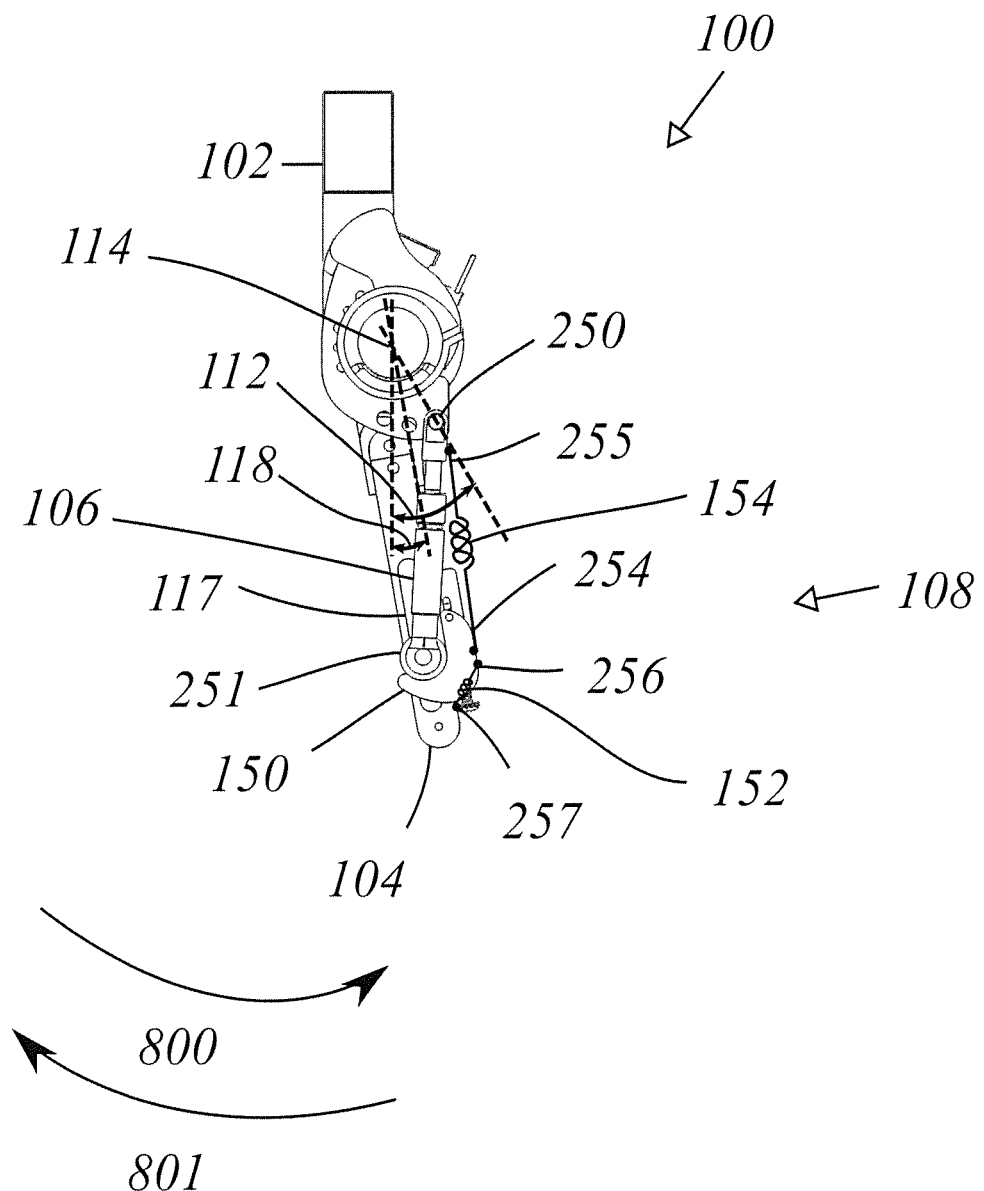
FIG. 30 shows an embodiment of the invention in practice where release mechanism 108 is in its first operational mode such that knee angle 118 is smaller than toggle angle 112.
Figure 31:
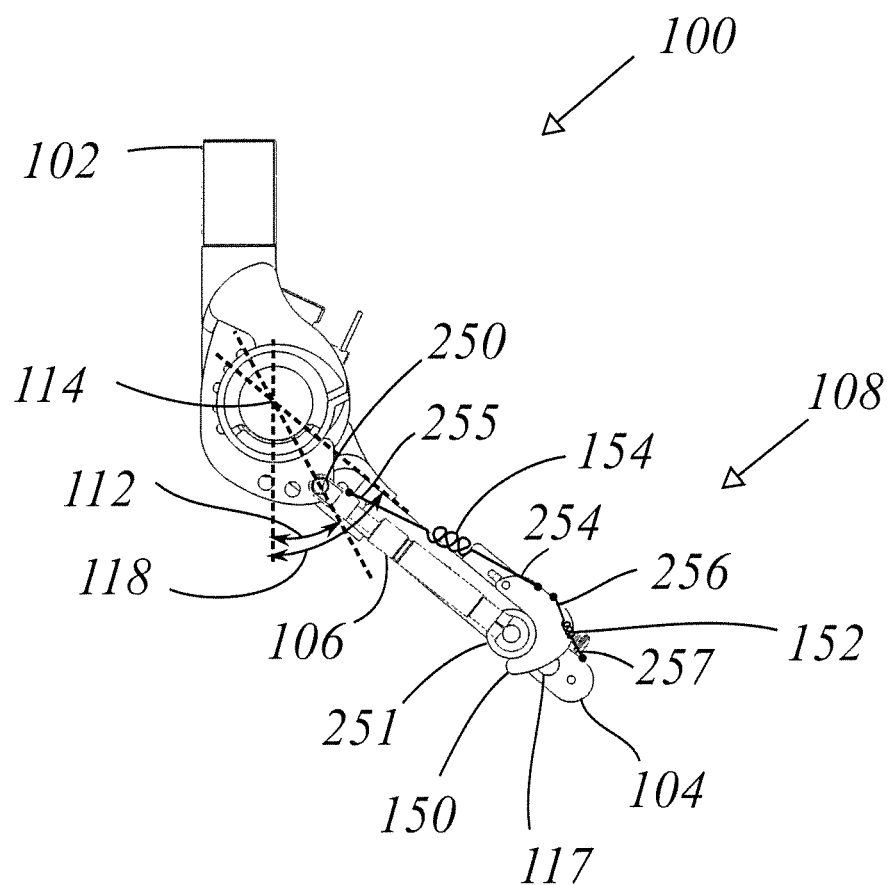
FIG. 31 shows an embodiment of the invention in practice where release mechanism 108 is in its first operational mode such that knee angle 118 is larger than toggle angle 112.

FIG. 30 shows an embodiment of the invention in practice where release mechanism 108 is in its first operational mode such that knee angle 118 is smaller than toggle angle 112, and force generator 106 produces a torque that resists flexion of shank link 104 relative to thigh link 102. FIG. 31 shows an embodiment of the invention in practice where release mechanism 108 is in its first operational mode such that knee angle 118 is larger than toggle angle 112, and the force generator 106 produces a torque that encourages flexion of shank link 104 relative to thigh link 102.

Figure 34:
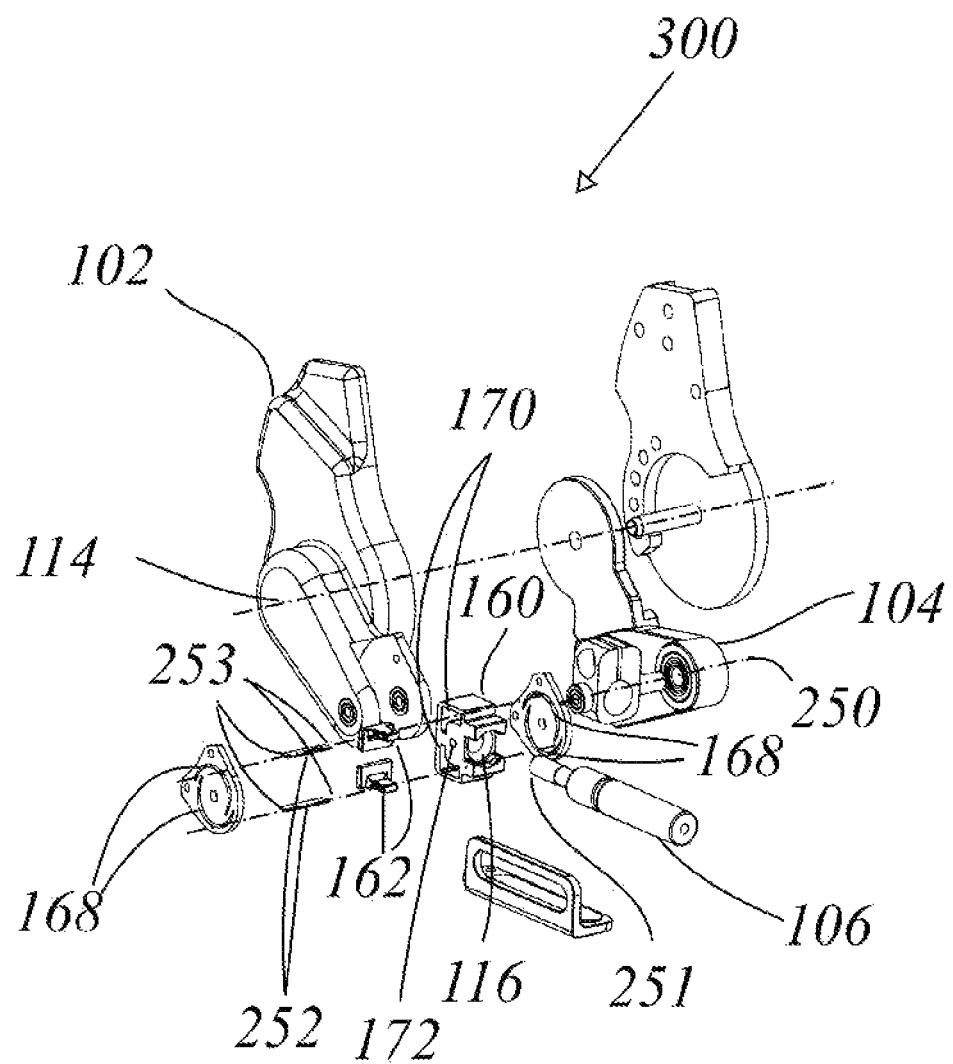
FIG. 34 shows the explosion view of the second embodiment in practice.
Figure 35:
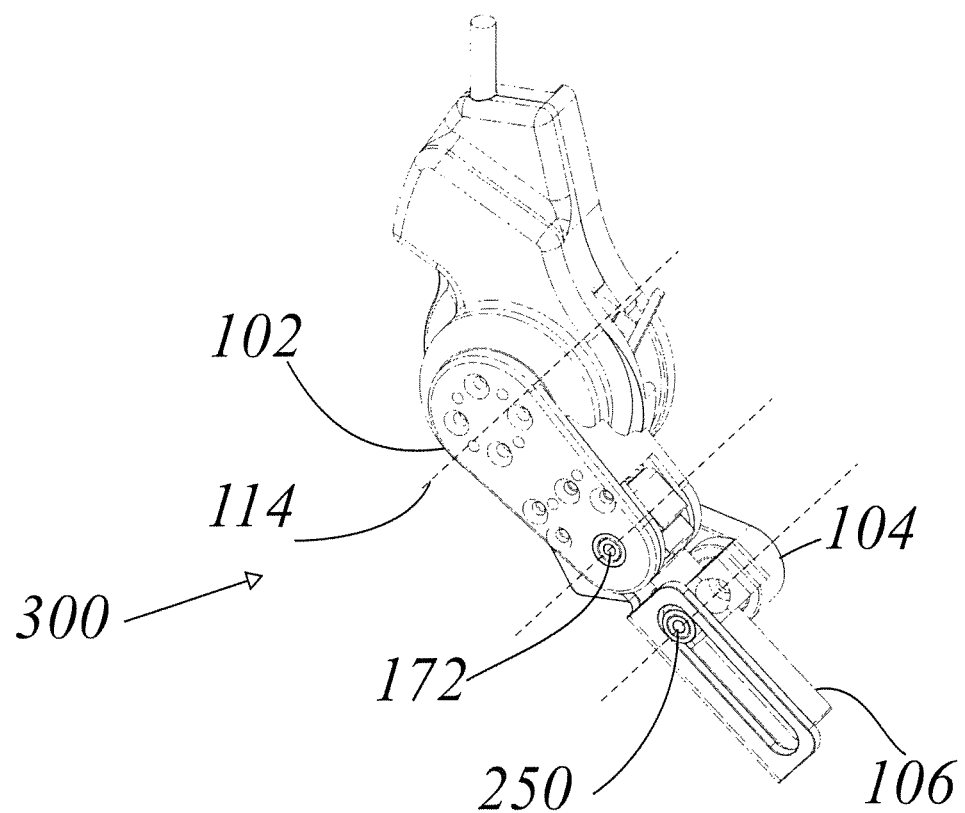
FIG. 35 shows the invention further comprising another exoskeleton knee design.
Figure 36:
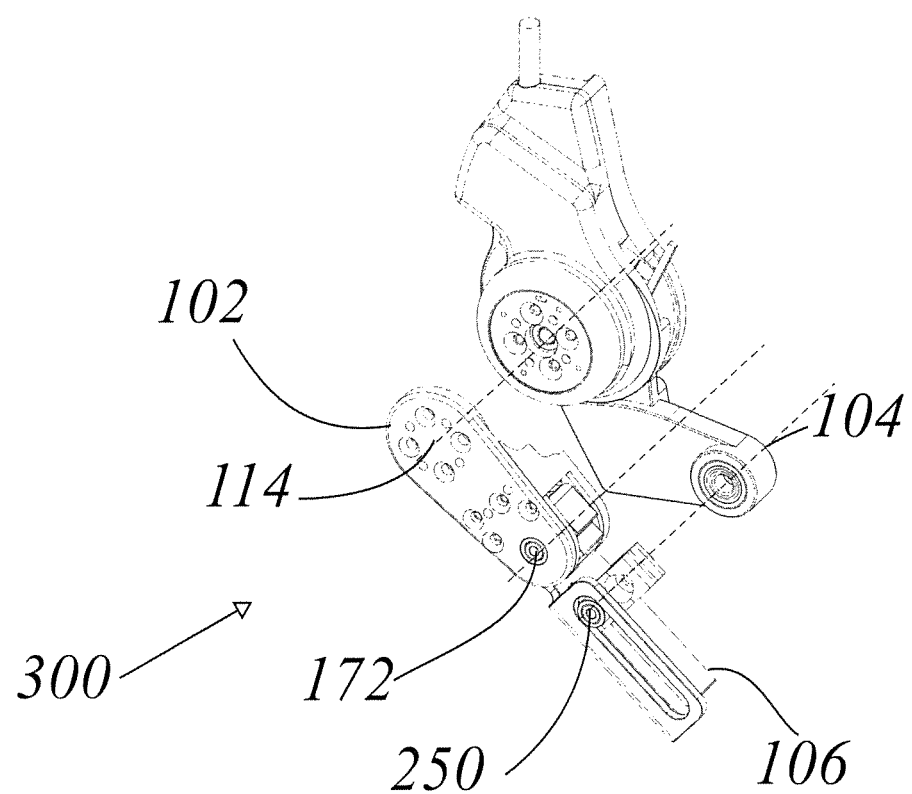
FIG. 36 shows the explosion view of the invention further comprising another exoskeleton knee design.
Figure 37:
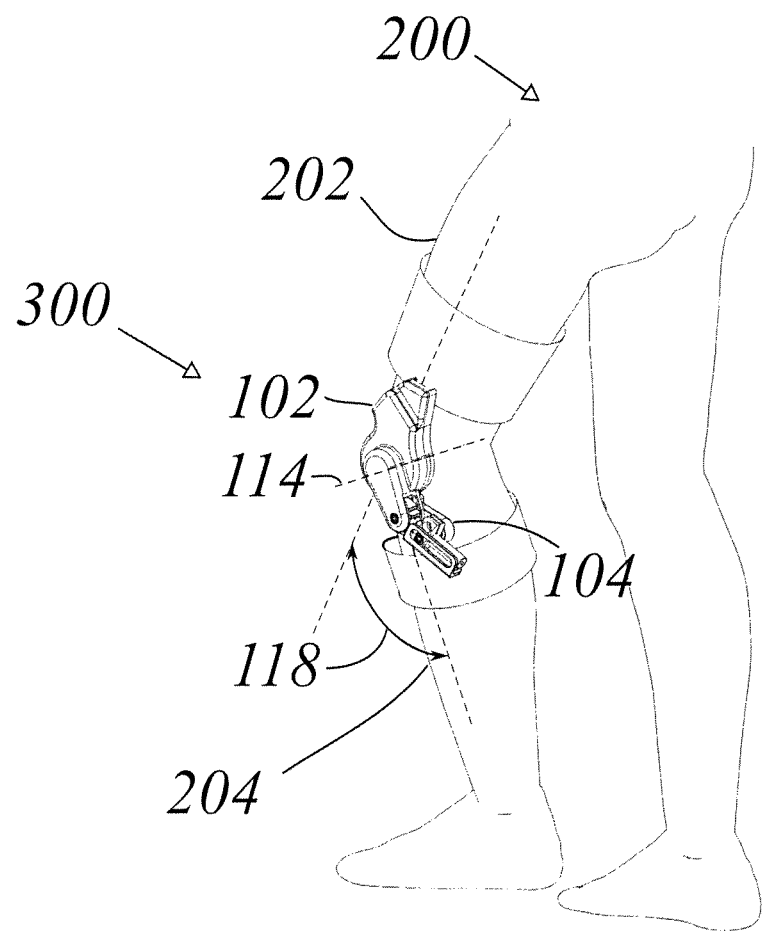
FIG. 37 shows the second embodiment of the invention wearing by a person 200.

FIG. 33 shows one embodiment of the passive power-conservative artificial knee 300 in practice. FIG. 34 shows the explosion view of one embodiment of the passive power-conservative artificial knee 300 in practice. FIG. 35 shows one embodiment of the passive power-conservative artificial knee 300 further comprising another exoskeleton knee design. FIG. 36 shows the explosion view of one embodiment of the passive power-conservative artificial knee 300 further comprising another exoskeleton knee design. FIG. 37 shows one embodiment of the passive power-conservative artificial knee 300 wearing by a person 200.

Figure 38:
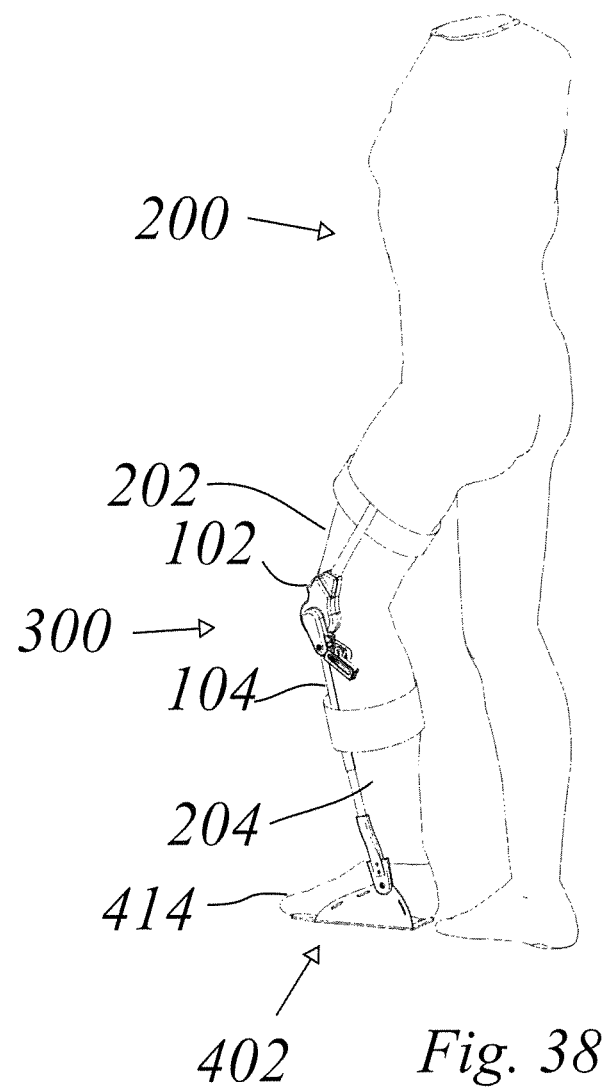
FIG. 38 shows an embodiment of the invention further comprising a ankle-foot orthosis 402.

FIG. 38 depicts an embodiment of the invention wherein the passive power-conservative artificial knee 300 further comprises an ankle-foot orthosis 402. In some embodiments of the invention, such as the embodiment shown in FIG. 38, an ankle-foot orthosis 402 is capable of being coupled to person's foot. In some embodiments of the invention, ankle-foot orthosis 402 is connectable to shank link 104. In some embodiments of the invention, passive power-conservative artificial knee 300 further comprises an ankle-foot-orthosis, which is worn outside the wearer's shoes. In some embodiments of the invention, passive power-conservative artificial knee 300 further comprises an ankle-foot-orthosis, which is worn inside the wearer's shoe like an insole (the wearer's shoes are not shown for clarity). An ordinary person skilled in the art can arrive at many forms of internal and external ankle-foot-orthoses.

In some embodiments of the invention, passive power-conservative artificial knee 300 further comprises an ankle-foot-orthosis, which is a standard short leg ankle-foot-orthosis (AFO) with fixed (but sometimes adjustable) hinge. This type of AFO is relatively light and easy to fit into shoes. This AFO keeps the foot at any desired angle relative to shank link 104. Further, this AFO does not allow plantar flexion or dorsiflexion, so it doesn't provide quite as natural of a gait as do some other braces. In some embodiments of the invention passive power-conservative artificial knee 300 further comprises an ankle-foot-orthosis, which is a standard solid ankle-foot-orthosis. This type of ankle-foot-orthosis stops plantarflexion and also stops or limits dorsiflexion. In some embodiments of the invention passive power-conservative artificial knee 300 further comprising an ankle-foot-orthosis, which is a Plantarflexion Stop AFO. This AFO acts to stop plantarflexion by not letting the foot link point downwards. This type of AFO has a hinge that allows for normal dorsiflexion of foot.

It should be appreciated that, although specific examples of different ankle-foot orthosis are shown, there are other types of ankle-foot-orthosis that could be utilized with the present invention. For example, in some embodiments of the invention, ankle-foot-orthosis is a Dorsiflexion Assist AFO (not shown). This type of AFO has a spring-like hinge that acts to raise the foot link (dorsiflex the ankle) when the foot comes off of the ground. The Dorsiflexion Assist AFO offers the advantage of a more normal gait pattern. In some embodiments of the invention, the ankle-foot-orthosis is a standard Posterior Leaf Spring ankle-foot-orthosis (not shown). In some embodiments of the invention, the ankle-foot-orthosis is an Energy Return ankle-foot-orthosis (not shown). This type of AFO uses a natural flex built into the material of the AFO to provide assistance in dorsiflexion. These devices are often made of carbon graphite materials. In general, the ankle-foot-orthosis of the present invention comprises any device or combination of internal or external ankle-foot-orthosis capable of performing the indicated functions. Examples of external or internal ankle-foot-orthosis include, without limitation, flexible AFO, rigid AFO, AFO with tamarack flexure, AFO with anti-talus, AFO anti-talus (anterior shell or shell in the front), AFO with a free-motion ankle joint, AFO with an adjustable rigid ankle joint, AFO with a spring-loaded ankle joint, AFO with an adjustable spring-loaded ankle joint and combinations thereof.

Figure 39:
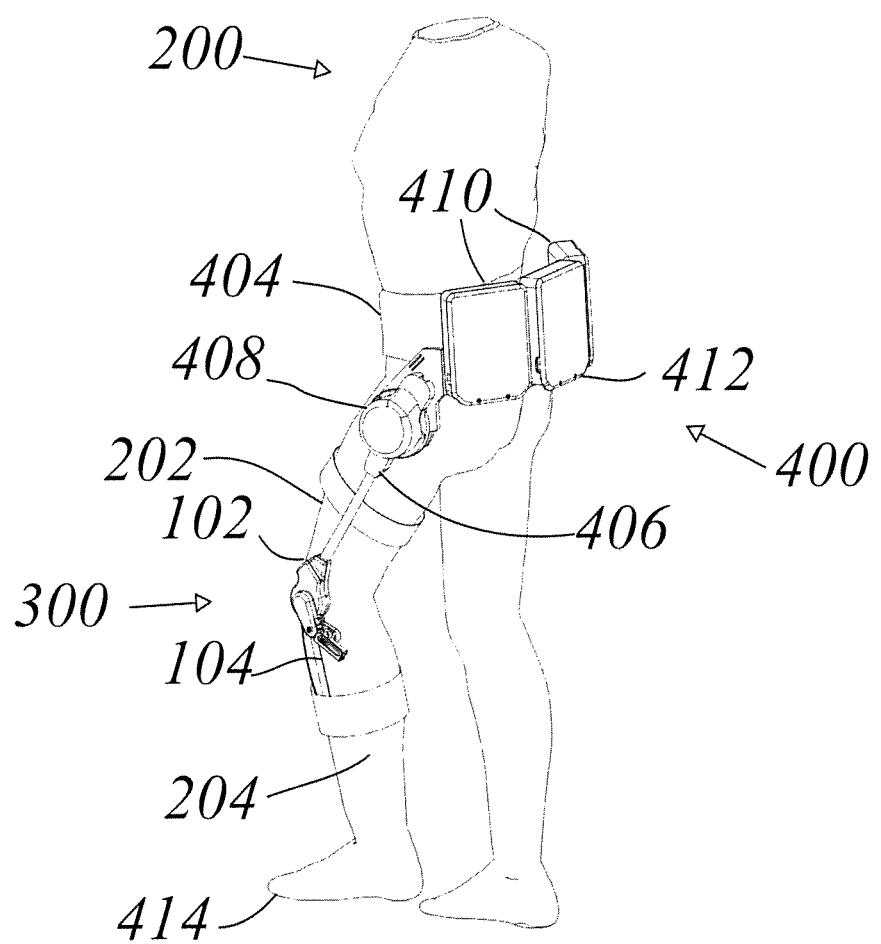
FIG. 39 shows an embodiment of the invention further comprising an exoskeleton trunk 400.

FIG. 39 shows an embodiment of the invention where passive power-conservative artificial knee 300 further comprises an exoskeleton trunk 400. Exoskeleton trunk 400 is configurable to be coupled to the person's upper body. In some embodiments of the invention, exoskeleton trunk 400 is coupled to a person like a backpack (not shown). In some embodiments of the invention, exoskeleton trunk 400 is coupled to a person like a belt, as depicted in FIG. 39, for example. Exoskeleton trunk 400 comprises a torso link 404 capable of being coupled to person's upper body and torso. Exoskeleton trunk 400 further comprises a trunk thigh link 406 configurable to rotatably couple thigh link 102 to torso link 404. In some embodiments of the invention, trunk thigh link 406 is coupled to thigh link 102. In some embodiments of the invention, trunk thigh link 406 is not coupled to thigh link 102. In an alternative embodiment not shown, trunk thigh link 406 is coupled to user's thigh 202. In some embodiments of the invention, exoskeleton trunk 400 further comprises an actuator 408 capable of providing torque between torso link 404 and trunk thigh link 406. The controller box 410 and the batteries 412 for the actuators are shown in FIG. 39.

Figure 40:
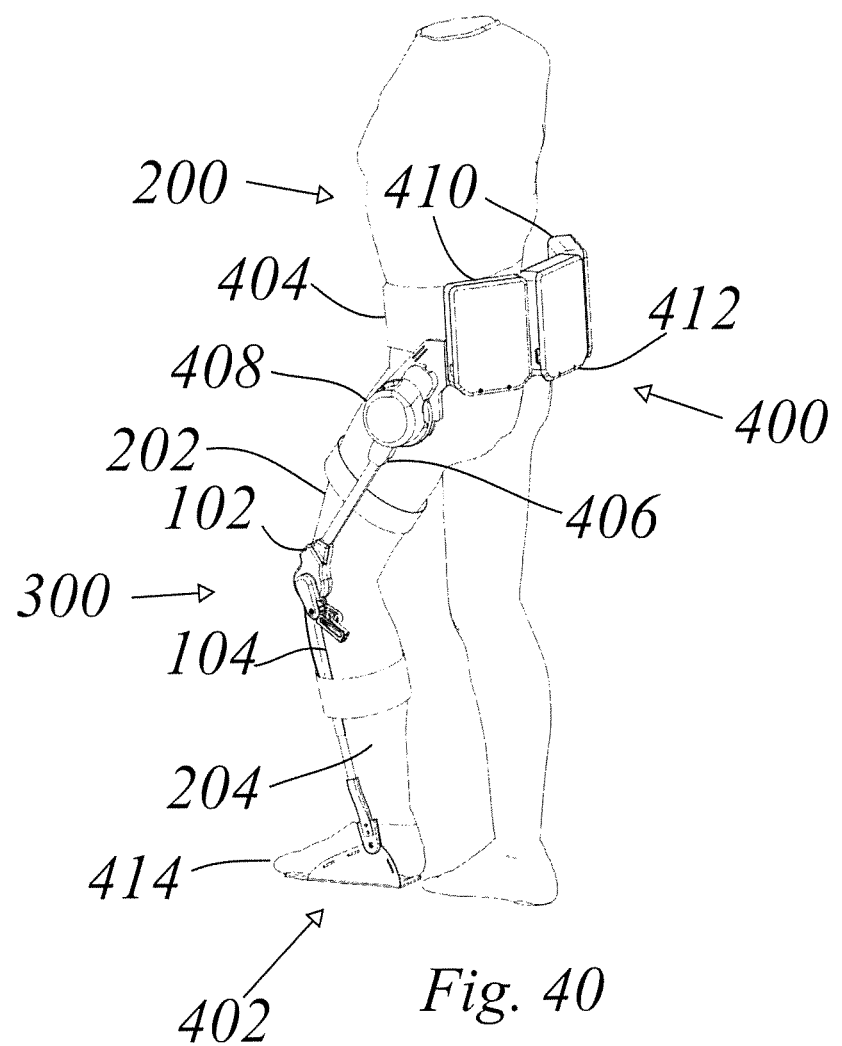
FIG. 40 shows an embodiment of the invention further comprising an exoskeleton trunk including the ankle foot orthosis 402.

FIG. 40 depicts embodiment of the present invention (passive power-conservative artificial knee 300) including both an exoskeleton trunk 400 and an ankle-foot orthosis (e.g., 402). In the embodiment shown, the ankle-foot orthosis 402 of the present invention is capable of being coupled to user's foot 414 and is connectable to shank link 104. Alternatively, ankle-foot-orthosis is worn outside the wearer's shoes. In some embodiments of the invention, ankle-foot-orthosis 402 is worn inside the wearer's shoe like an insole. An ordinary person skilled in the art can arrive at many forms of internal and external ankle-foot-orthoses. In some embodiments of the invention passive power-conservative artificial knee 300 further comprising an ankle-foot-orthosis, which is a standard short leg ankle-foot-orthosis (AFO) with fixed (but sometimes adjustable) hinge. This type of AFO is relatively light and easy to fit into shoes. This AFO keeps the foot at any desired angle relative to shank link 104. Further, this AFO does not allow plantar flexion or dorsiflexion, so it doesn't provide quite as natural of a gait as do some other braces. In some embodiments of the invention passive power-conservative artificial knee 300 further comprises an ankle-foot-orthosis, which is a standard solid ankle-foot-orthosis. This type of ankle-foot-orthosis stops plantarflexion and also stops or limits dorsiflexion. In some embodiments of the invention passive power-conservative artificial knee 300 further comprising an ankle-foot-orthosis, which is a Plantarflexion Stop AFO. This AFO acts to stop plantarflexion by not letting the foot link point downwards. This type of AFO has a hinge that allows for normal dorsiflexion of foot. Exoskeleton trunk 400 is configurable to be coupled to the person's upper body. In some embodiments of the invention, exoskeleton trunk 400 is coupled to a person like a backpack using shoulder straps. In some embodiments of the invention as shown in FIG. 40, exoskeleton trunk 400 is coupled to a person like a belt.

Figure 41:
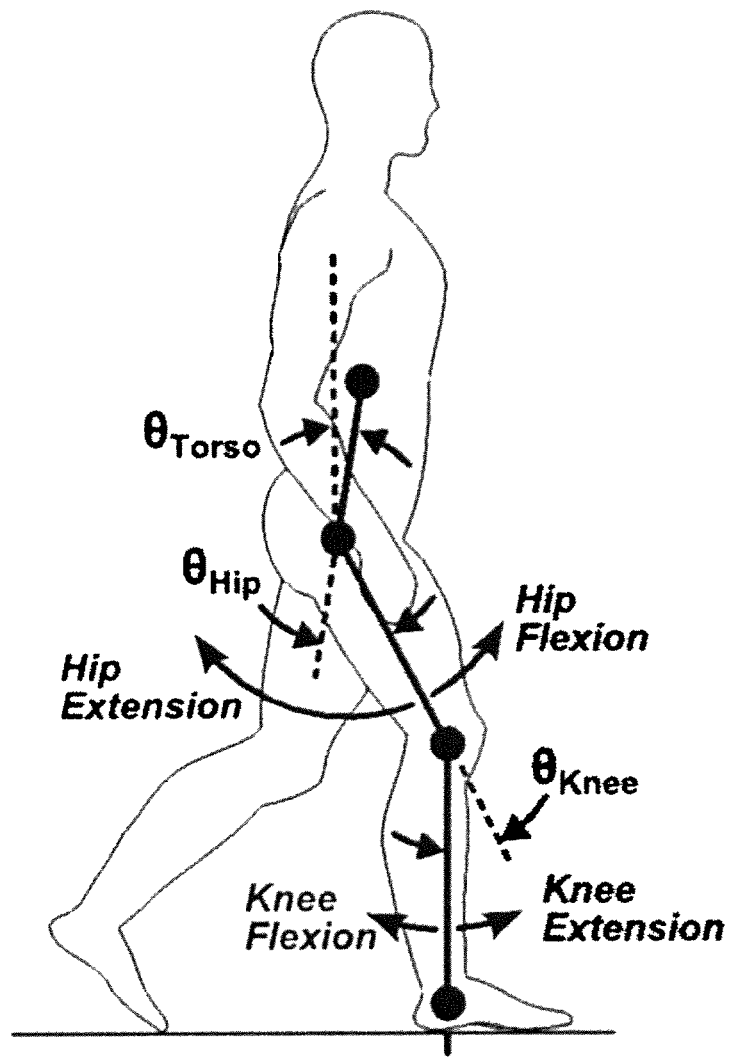
FIG. 41 shows the biomimetic definition of human joint angles.
Figure 42:
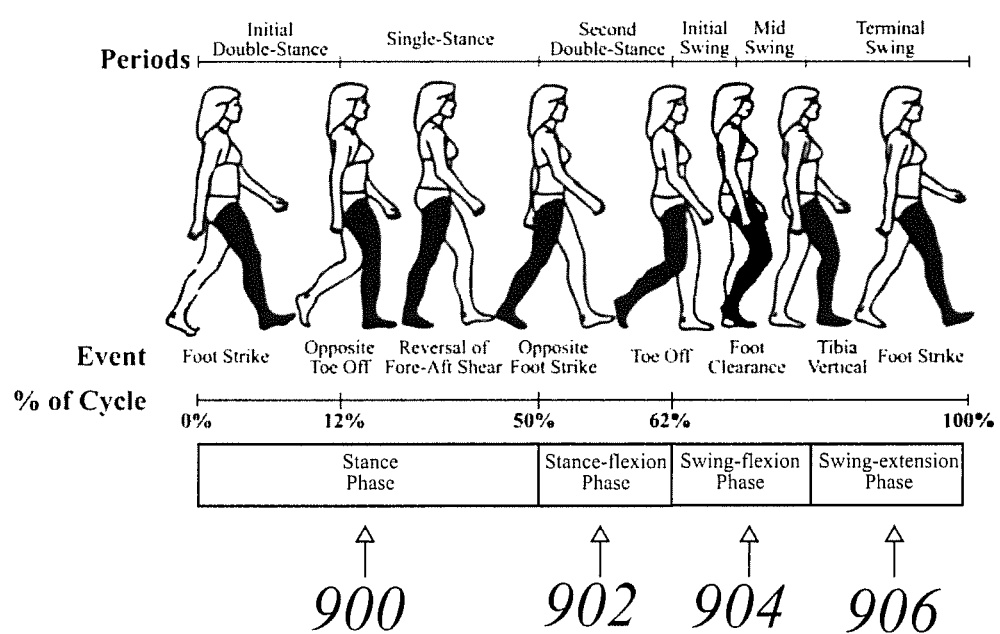
FIG. 42 shows gait phases in a gait cycle.

FIG. 41 shows the biomimetic definition of hip flexion, hip extension, knee flexion, knee extension, hip angle, and knee angle. FIG. 42 shows gait phases in a gait cycle. Stance phase 900 is from foot strike to opposite foot strike; stance-flexion phase 902 is from opposite foot strike to toe off; swing-flexion phase 904 is from toe off to maximum knee flexion; swing extension 906 is from maximum knee flexion to foot strike. The configuration where force generator 106 produces a torque that resists flexion of shank link 104 relative to thigh link 102 is designed to lie in stance phase 900 and some portion of stance-flexion phase 902. The configuration where force generator 108 produces a torque that encourages flexion of shank link 104 relative to thigh link 102 is designed to lie in some portion of stance-flexion phase 902 and some portion of swing-flexion phase 904. The configuration where the release mechanism 108 is in its second operational mode is designed to lie in some portion of swing-flexion phase 904 and swing-extension phase 906.

What is claimed is:

1. A passive power-conservative artificial knee comprising:
   a first link;
   a second link, rotatably coupled to said first link at a knee joint,
      wherein the first link is one of a thigh link or a shank link, and wherein the second link is another one of the thigh link or the shank link;
   a passive compressive force generator, comprising a first end and a second end,
      said passive compressive force generator rotatably coupled to said second link from the first end;
   a release mechanism, coupled to said first link,
      wherein said release mechanism comprises a first operational mode and a second operational mode,
      wherein, in the first operational mode, said release mechanism is configured to couple the second end of said passive compressive force generator to said first link, and, in the second operational mode, said release mechanism is configured such that said second end of said passive compressive force generator is not coupled to said first link, and
      wherein said release mechanism is configured to move into the first operational mode, thereby causing the passive compressive force generator to resist flexion of said first link relative to said second link when an angle of said knee joint is less than a toggle angle, and
      wherein said passive compressive force generator is configured to encourage flexion of said first link relative to said second link while said release mechanism is in said first operational mode when said angle of said knee joint is larger than said toggle angle, and
      wherein said release mechanism is configured to move into the second operational mode when a compressive force of the passive compressive force generator is substantially small and when said passive compressive force generator is substantially extended.

2. The passive power-conservative artificial knee of claim 1, wherein said first link is the thigh link and is configurable to move in unison with a thigh of a wearer, and wherein said second link is the shank link and is configurable to move in unison with a shank of the wearer.

3. The passive power-conservative artificial knee of claim 1, wherein said first link is the shank link and is configurable to move in unison with a shank of a wearer, and wherein said second link is the thigh link and is configurable to move in unison with a thigh of the wearer.

4. The passive power-conservative artificial knee of claim 1, wherein said first link comprises a first connector configured to couple said first link to a shank of a wearer and said second link includes a second connector configured to couple said second link to a thigh of the wearer.

5. The passive power-conservative artificial knee of claim 1, wherein said first link comprises a first connector configured to couple the first link to a thigh of a wearer, and wherein said second link comprises a second connector configured to couple the second link to a shank of the wearer.

6. The passive power-conservative artificial knee of claim 1, wherein said release mechanism comprises:
   a holding block, rotatably coupled to said first link;
   a constraint path, in said holding block, allowing for motion of said second end of said passive compressive force generator along the constraint path in the holding block;
   a moving block capable of blocking the motion of said second end of said passive compressive force generator in said holding block; and
   a trigger spring, comprising a first end and a second end, the trigger spring being coupled to said moving block from the first end of the trigger spring and to said first link from the second end of the trigger spring, wherein;
   when said release mechanism is in the first operational mode, said moving block is held stationary in a slot by a force of said passive compressive force generator while said trigger spring is pulled by the second end imposing a tensile force on said moving block;
   when said release mechanism is in the second operational mode, said moving block and said trigger spring move due to motion of said second link relative to said first link, and said moving block is not blocking motion of the second end of said passive compressive force generator.

7. The passive power-conservative artificial knee of claim 6, further comprising a cam slot on said first link;
   wherein said second end of said trigger spring is coupled to a guiding piece which moves in the cam slot; and wherein
   when the release mechanism is in the first operational mode and the second link flexes, said guiding piece moves along said cam slot, thereby increasing the tensile force; and
   when said release mechanism is in the second operational mode and said second link extends relative to said first link, said guiding piece moves along said cam slot, thereby pushing said moving block.

8. The passive power-conservative artificial knee of claim 1, wherein said release mechanism comprises:
   a hook rotatably, coupled to said first link;
   a constraint path, in said first link, the constraint path configured to allow motion of said second end of said passive compressive force generator along said constraint path;
   a trigger spring, comprising a first end and a second end, said trigger spring coupled to said hook from the first end of the trigger spring, and said trigger spring coupled to said second link from the second end of the trigger spring; and
   a return spring comprising a first end and a second end, said return spring coupled to said hook from the first end of the return spring, and said return spring coupled to said first link from the second end of the return spring; and
   wherein said trigger spring is configured to encourage transition of the release mechanism from said first operational mode to said second operational mode, and
   wherein said return spring is configured to encourage transition of the release mechanism from said second operational mode to said first operational mode.

9. The passive power-conservative artificial knee of claim 1, further comprising an ankle-foot orthosis capable of being coupled to a foot of a wearer.

10. The passive power-conservative artificial knee of claim 9, wherein said ankle-foot orthosis is connectable to said first link or said second link.

* * * * *